United States Patent
MacEwan et al.

(10) Patent No.: US 10,149,749 B2
(45) Date of Patent: Dec. 11, 2018

(54) BIOMEDICAL PATCHES WITH ALIGNED FIBERS

(75) Inventors: Matthew R. MacEwan, St. Louis, MO (US); Jingwei Xie, Chesapeake, OH (US); Zack Ray, St. Louis, MO (US); Younan Xia, Atlanta, GA (US)

(73) Assignee: Washington University, St. Louis, MO (US)

( * ) Notice: Subject to any disclaimer, the term of this patent is extended or adjusted under 35 U.S.C. 154(b) by 1162 days.

(21) Appl. No.: 13/703,210

(22) PCT Filed: Jun. 16, 2011

(86) PCT No.: PCT/US2011/040691
§ 371 (c)(1),
(2), (4) Date: Mar. 20, 2013

(87) PCT Pub. No.: WO2011/159889
PCT Pub. Date: Dec. 22, 2011

(65) Prior Publication Data
US 2013/0197663 A1    Aug. 1, 2013

Related U.S. Application Data

(60) Provisional application No. 61/355,712, filed on Jun. 17, 2010.

(51) Int. Cl.
| | | |
|---|---|---|
| *D01D 5/12* | (2006.01) | |
| *A61F 2/02* | (2006.01) | |
| *A61L 15/22* | (2006.01) | |
| *A61L 15/42* | (2006.01) | |
| *A61L 27/14* | (2006.01) | |

(Continued)

(52) U.S. Cl.
CPC .............. *A61F 2/02* (2013.01); *A61L 15/22* (2013.01); *A61L 15/42* (2013.01); *A61L 27/14* (2013.01);

(Continued)

(58) Field of Classification Search
CPC ........................ D01D 5/0076; D01D 5/0092
See application file for complete search history.

(56) References Cited

U.S. PATENT DOCUMENTS

| | | | |
|---|---|---|---|
| 3,280,229 A | 10/1966 | Simons | |
| 4,738,740 A | * 4/1988 | Pinchuk | .................... A61F 2/06 |
| | | | 156/167 |

(Continued)

FOREIGN PATENT DOCUMENTS

| | | |
|---|---|---|
| WO | 0127365 A1 | 4/2001 |
| WO | 2004016839 A1 | 2/2004 |

(Continued)

OTHER PUBLICATIONS

Park, S. et al., Apparatus for Preparing Electrospun Nanofibers: Designing and Electrospinning process for Nanofiber Fabrication, Polymer International, 2007, pp. 1361-1366.

*Primary Examiner* — Yogendra N Gupta
*Assistant Examiner* — Joseph S Leyson
(74) *Attorney, Agent, or Firm* — Armstrong Teasdale LLP

(57) ABSTRACT

A structure of aligned (e.g., radially and/or polygonally aligned) fibers, and systems and methods for producing and using the same. One or more structures provided may be created using an apparatus that includes one or more first electrodes that define an area and/or partially circumscribe an area. For example, a single first electrode may enclose the area, or a plurality of first electrode(s) may be positioned on at least a portion of the perimeter of the area. A second electrode is positioned within the area. Electrodes with rounded (e.g., convex) surfaces may be arranged in an array, and a fibrous structure created using such electrodes may include an array of wells at positions corresponding to the positions of the electrodes.

24 Claims, 23 Drawing Sheets

(51) Int. Cl.
  *A61L 27/50* (2006.01)
  *D01D 5/00* (2006.01)
  *D04H 1/728* (2012.01)
  *D04H 3/016* (2012.01)
  *D04H 3/073* (2012.01)
  *B29C 47/00* (2006.01)
  *C12M 1/12* (2006.01)

(52) U.S. Cl.
  CPC .......... *A61L 27/50* (2013.01); *B29C 47/0014* (2013.01); *B29C 47/0076* (2013.01); *D01D 5/0076* (2013.01); *D01D 5/0092* (2013.01); *D04H 1/728* (2013.01); *D04H 3/016* (2013.01); *D04H 3/073* (2013.01); *C12M 25/14* (2013.01)

(56) References Cited

U.S. PATENT DOCUMENTS

| | | |
|---|---|---|
| 2005/0104258 A1 | 5/2005 | Lennhoff |
| 2006/0264140 A1 | 11/2006 | Andrady |
| 2007/0152378 A1* | 7/2007 | Kim ................ D01D 5/0076 264/465 |
| 2010/0092687 A1 | 4/2010 | Sumida et al. |

FOREIGN PATENT DOCUMENTS

| | | |
|---|---|---|
| WO | 2006096791 A2 | 9/2006 |
| WO | 2006123858 A1 | 11/2006 |
| WO | 2007086910 A2 | 8/2007 |
| WO | 20110095141 A1 | 8/2011 |

\* cited by examiner

FIG. 14A
Radially aligned
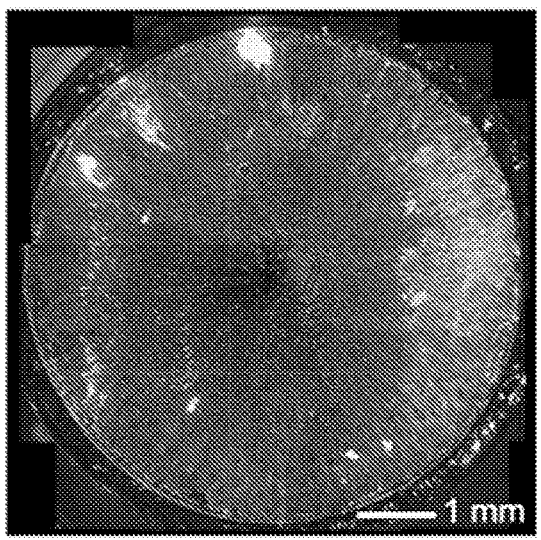
FIG. 14B
Random
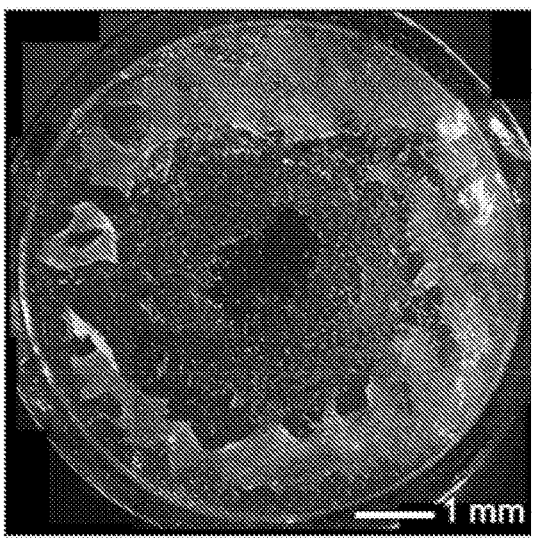
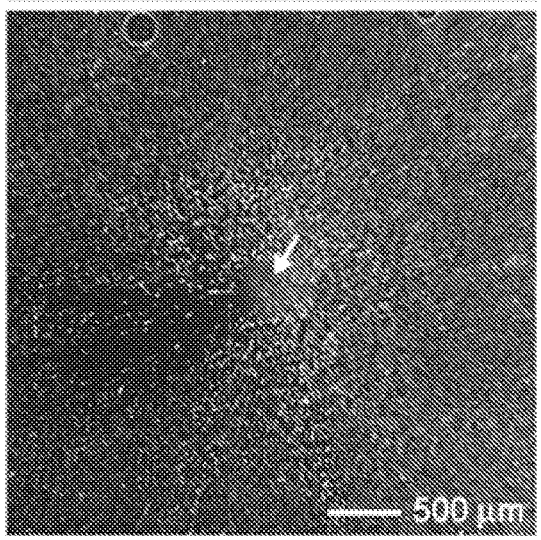
FIG. 14C
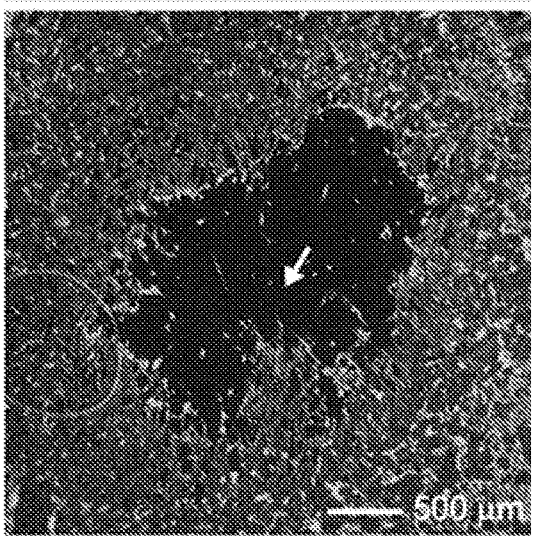
FIG. 14D FIG. 16A
Radially aligned
FIG. 16B
Random
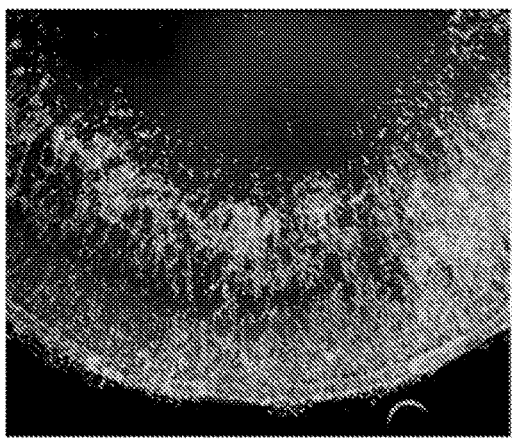
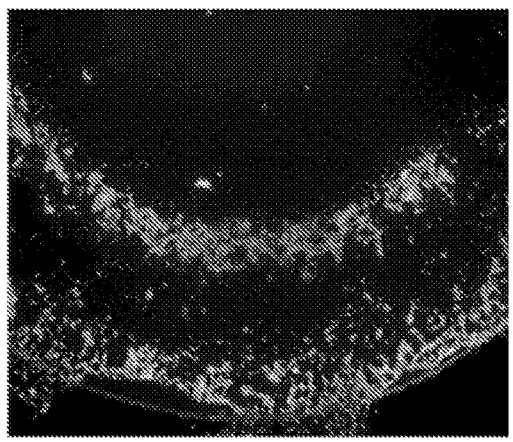
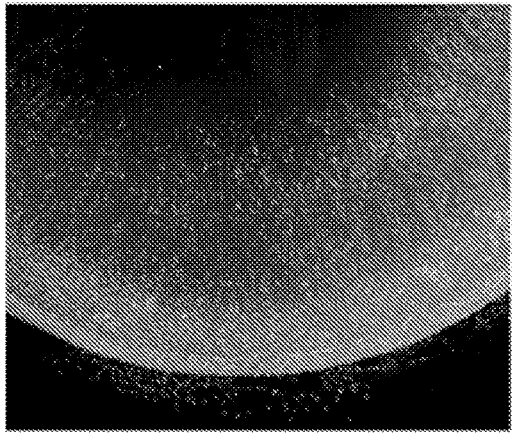
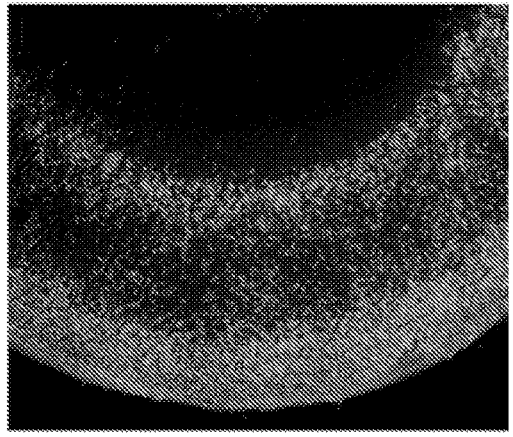
— 500 μm
FIG. 16C
FIG. 16D FIG. 17A
FIG. 17B
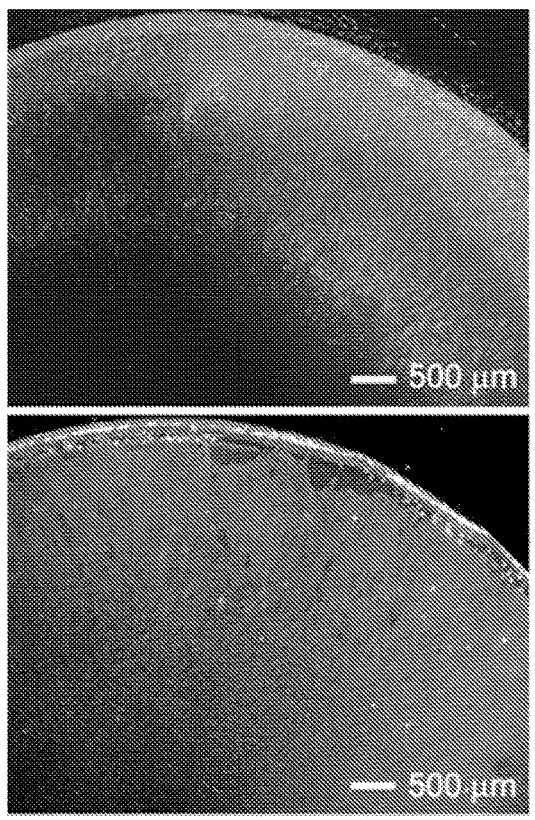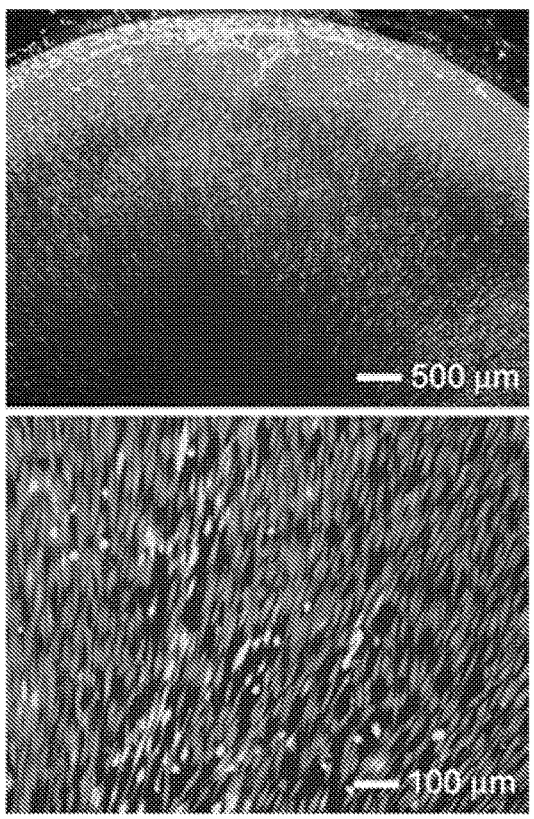
FIG. 17C
FIG. 17D
FIG. 18
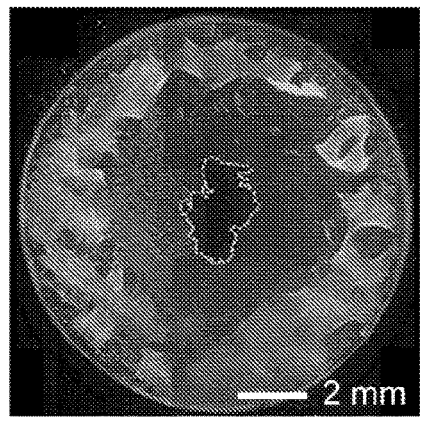

FIG. 20A
FIG. 20B
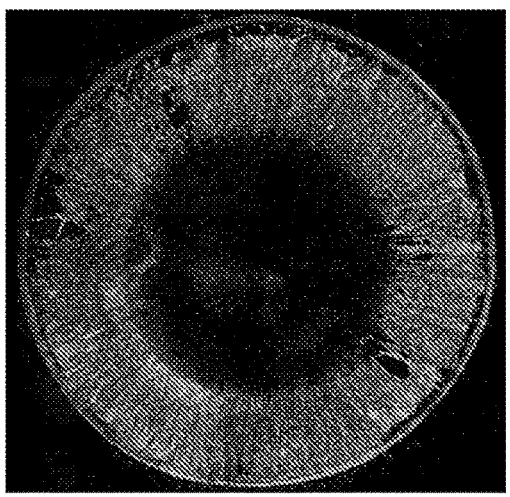
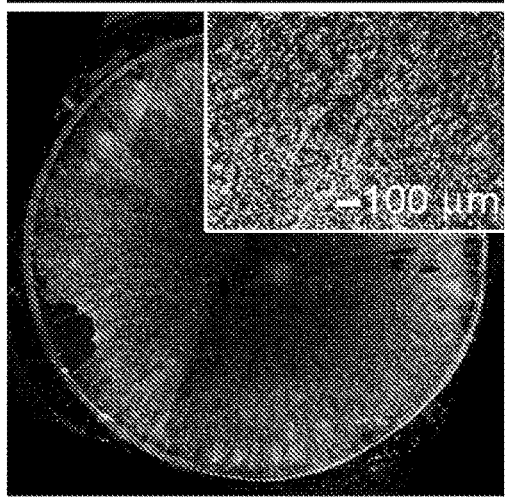
—— 1mm
FIG. 20C
FIG. 20D FIG. 21A
FIG. 21B
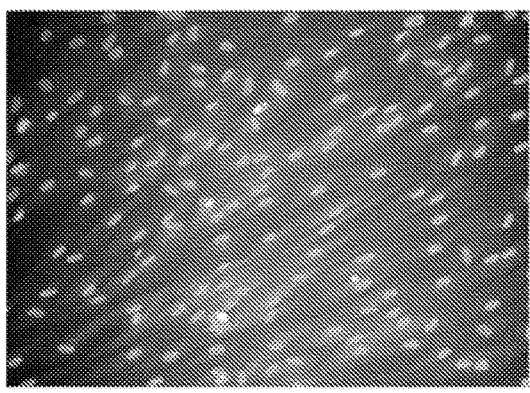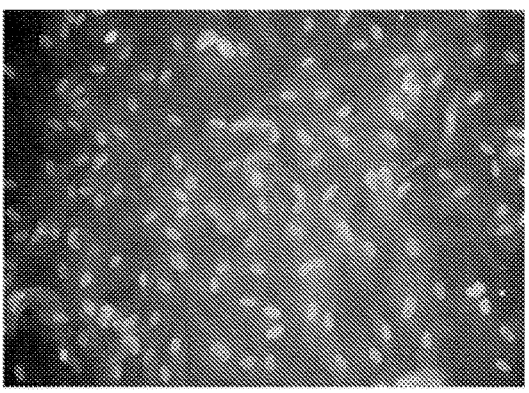
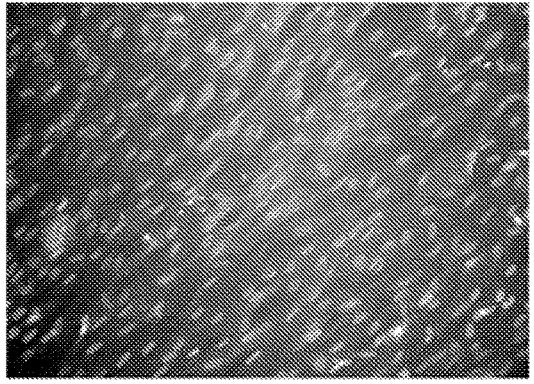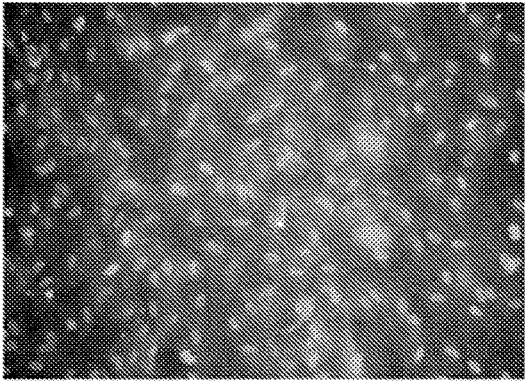
— 50 μm
FIG. 21C
FIG. 21D

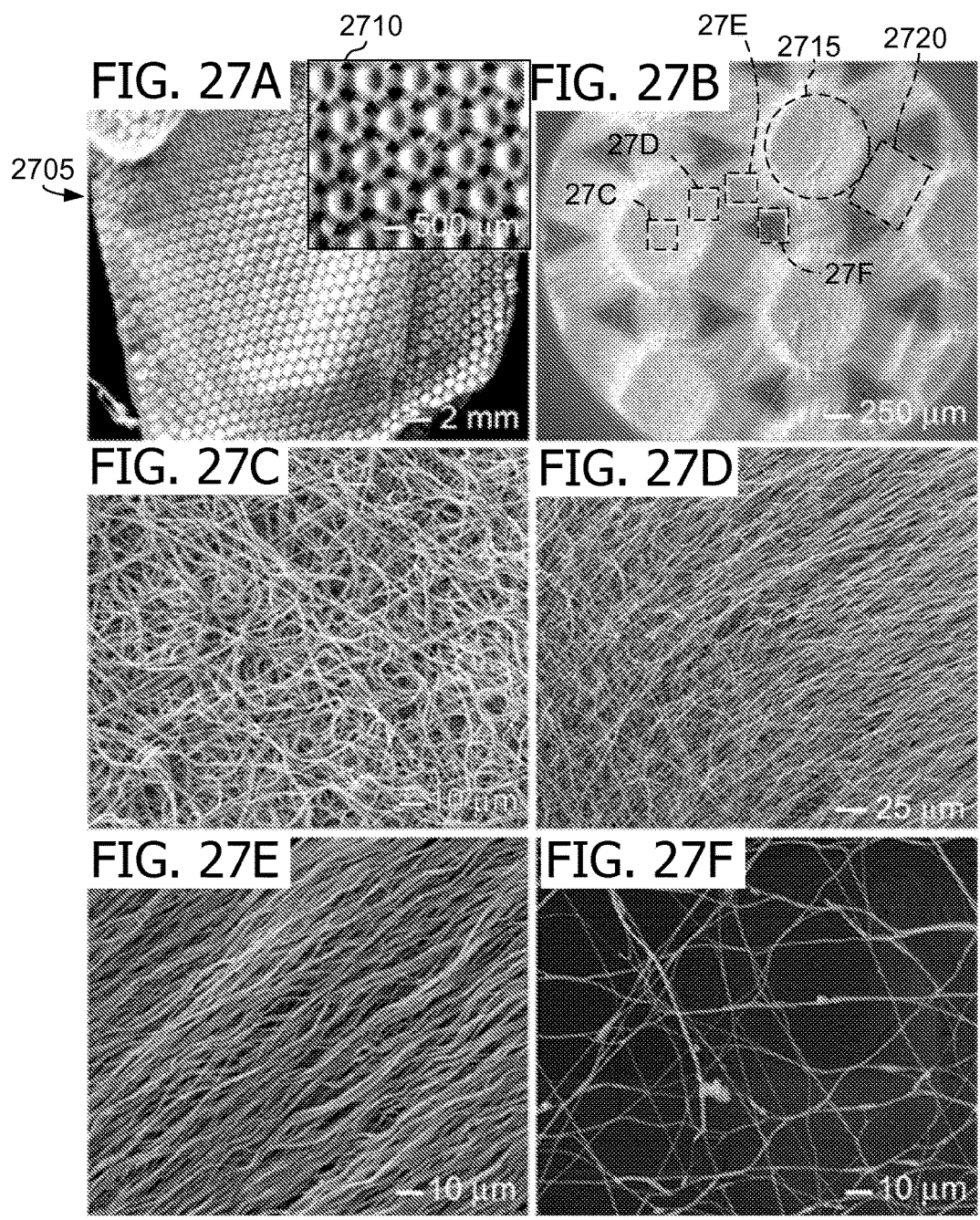

FIG. 28A
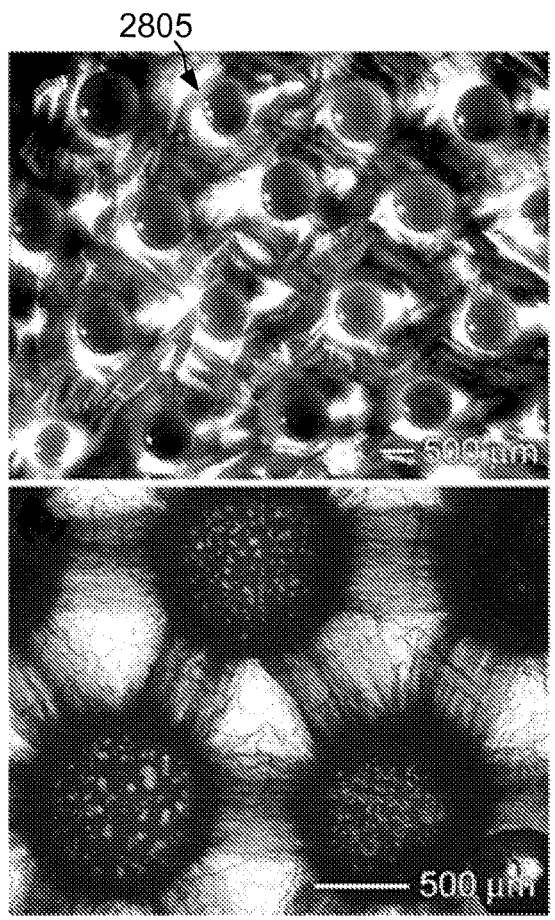
FIG. 28B
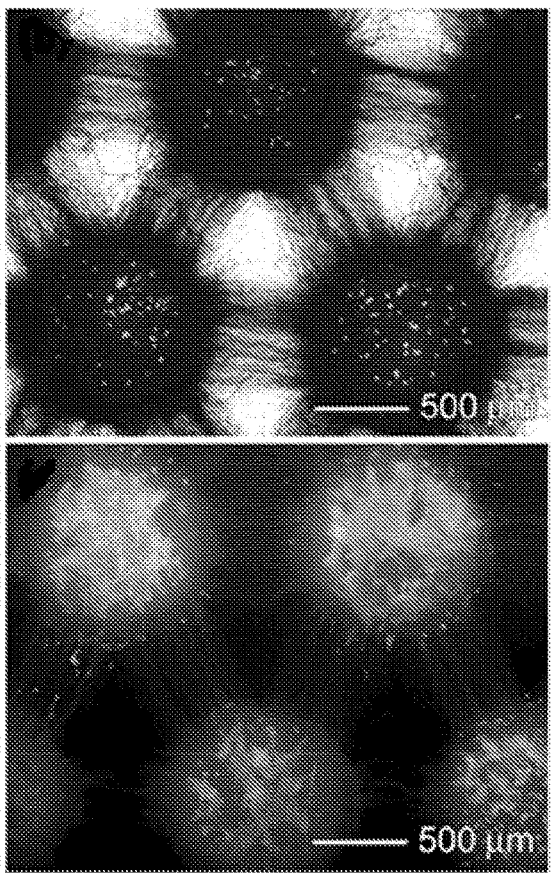
FIG. 28C
FIG. 28D
FIG. 29A
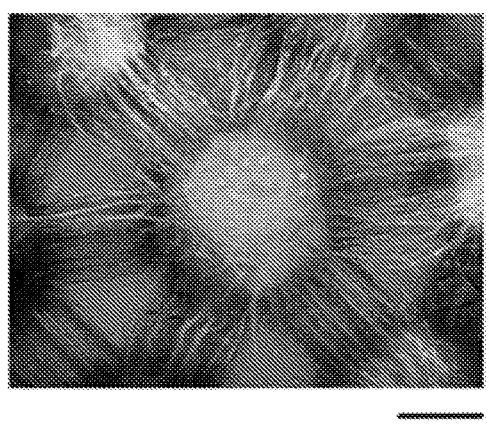
FIG. 29B
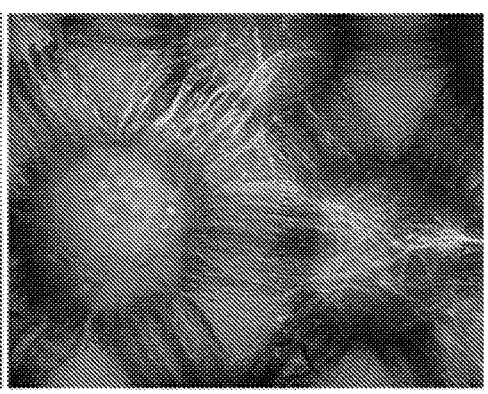

—— 500 μm

FIG. 31A            FIG. 31B
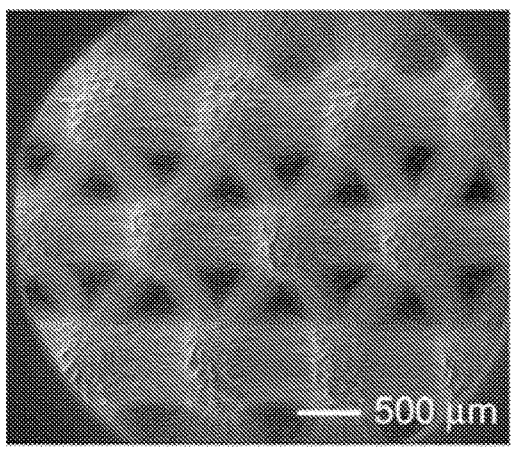 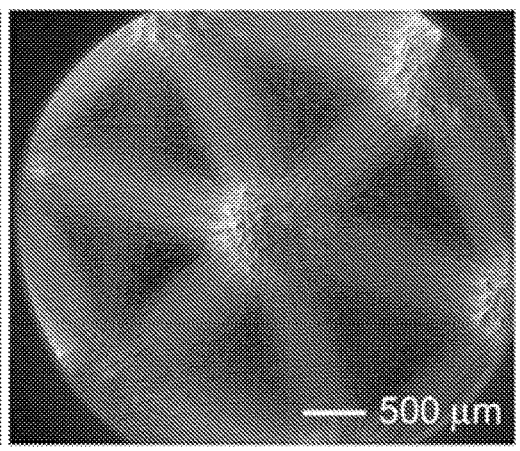
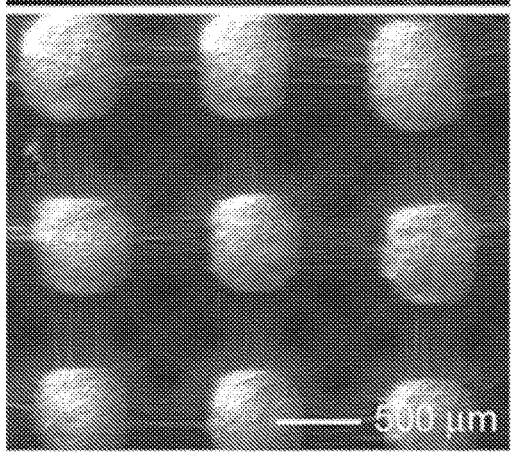 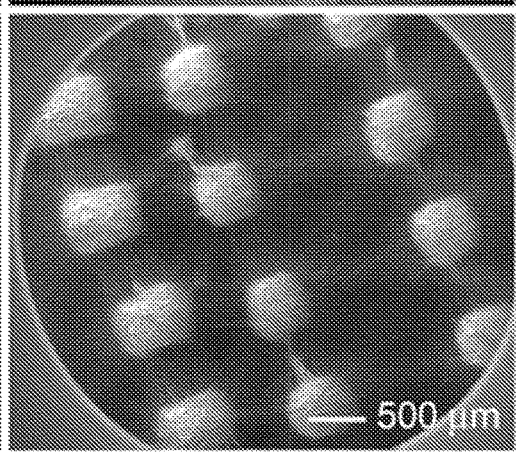
FIG. 31C            FIG. 31D

BIOMEDICAL PATCHES WITH ALIGNED FIBERS

CROSS-REFERENCE TO RELATED APPLICATIONS

This application is a 35 U.S.C. § 371 national stage application of PCT/US2011/040691, filed Jun. 16, 2011, which claims the benefit of U.S. Provisional No. 61/355,712, filed Jun. 17, 2010, the entireties of which are hereby incorporated by reference for all purposes.

STATEMENT REGARDING FEDERALLY SPONSORED RESEARCH & DEVELOPMENT

This invention was made with government support under Director's Pioneer Award DP1 OD000798-04, awarded by the U.S. National Institutes of Health, and Award No. ECS-0335765, awarded by the U.S. National Science Foundation. The government has certain rights in the invention.

BACKGROUND

Numerous surgical procedures result in the perforation or removal of biological tissue, such as the water-tight fibrous membrane surrounding the brain known as the dura mater. In some instances, such as minimally invasive neurosurgical procedures, relatively few small holes are created in the dura mater, while in others, such as the surgical resection of advanced tumors, large sections of the dura mater may be removed. In all of these cases, the tissue barrier surrounding the brain must be repaired in order to prevent damage to cortical tissues and leakage of cerebrospinal fluid. To facilitate this repair, neurosurgeons utilize sheets of polymeric materials or processed tissue that act like native dura, known as dural substitutes.

At least some known dural substitutes utilized in neurosurgical clinics are composed of an acellular collagen matrix obtained from isolated bovine or porcine tissues. While generally accepted in the field, such xenogenic dural substitutes may increase the incidence of adhesions and contractures, transmit various zoonotic diseases to patients, and generally reduce patient outcome following surgery. Furthermore, processed collagenous grafts are exceedingly expensive, costing patients and insurance companies thousands of dollars per procedure.

In addition while cell microarrays may be useful in biomedical research and tissue engineering, at least some known techniques for producing such cell microarrays may be costly and time consuming, and may require the use of specialized, sophisticated instrumentation.

SUMMARY

One or more embodiments described herein provide structures having a plurality of aligned (e.g., radially aligned and/or polygonally aligned) fibers. When such a structure is used as a biomedical patch, the alignment of fibers as described herein may provide directional cues that influence cell propagation. For example, the structures provided may promote new cell growth along the fibers, such that cell propagation in one or more desired directions may be achieved.

One or more structures provided may be created using an apparatus that includes one or more first electrodes that define an area and/or partially circumscribe an area. For example, a single first electrode may enclose the area, or a plurality of first electrode(s) may be positioned on at least a portion of the perimeter of the area. A second electrode is positioned within the area. In exemplary embodiments, when the electrodes are electrically charged at a first polarity, and a spinneret dispensing a polymer (e.g., toward the second electrode) is electrically charged at a second polarity opposite the first polarity, the dispensed polymer forms a plurality of fibers extending from the second electrode to the first electrodes. Further, electrodes with rounded (e.g., convex) surfaces may be arranged in an array, and a fibrous structure created using such electrodes may include an array of wells at positions corresponding to the positions of the electrodes.

This summary introduces a subset of concepts that are described in more detail below. This summary is not meant to identify essential features, and should not be read as limiting in any way the scope of the claimed subject matter.

BRIEF DESCRIPTION OF THE DRAWINGS

The embodiments described herein may be better understood by referring to the following description in conjunction with the accompanying drawings.

FIGS. 14A-14D are fluorescence micrographs comparing the migration of cells when dura tissues were cultured on scaffolds of radially aligned nanofibers and randomly oriented nanofibers for 4 days.

FIGS. 16A-16D are fluorescence micrographs showing cell morphology and distribution on scaffolds of radially aligned nanofibers and randomly oriented nanofibers with and without fibronectin coating after incubation for 1 day.

FIGS. 17A-17D are fluorescence micrographs showing the migration of dura fibroblasts seeded on fibronectin-coated scaffolds of radially aligned nanofibers for 1 day, 3 days, and 7 days.

FIG. 18 is an illustration of a method utilized to determine the area of remaining acellular region of the nanofiber scaffolds within the simulated tissue defect.

FIGS. 20A-20D are fluorescence micrographs showing live dural fibroblasts labeled with membrane dye on scaffolds of radially aligned nanofibers with fibronectin coating after a 1-day culture, a 3-day culture, a 7-day culture, and a 10-day culture.

FIGS. 21A-21D are fluorescence micrographs demonstrating the organization of cells and extracellular matrix adherent on scaffolds of radially aligned fibers and randomly oriented fibers obtained by immunostaining for type I collagen (green) and cell nuclei (blue).

FIGS. 27A-27F are microscopy images of a membrane produced using a collector with an array of electrodes, such as the collector shown in FIG. 24.

FIGS. 28A-28D are microscopy images illustrating cell growth in a membrane such as the membrane shown in FIGS. 27A-27F.

FIGS. 29A and 29B are microscopy images illustrating neurite propagation in a membrane such as the membrane shown in FIGS. 27A-27F.

FIGS. 31A-31D are scanning electron microscopy images illustrating membranes produced using a variety of electrode arrays.

DETAILED DESCRIPTION

Figure 1:
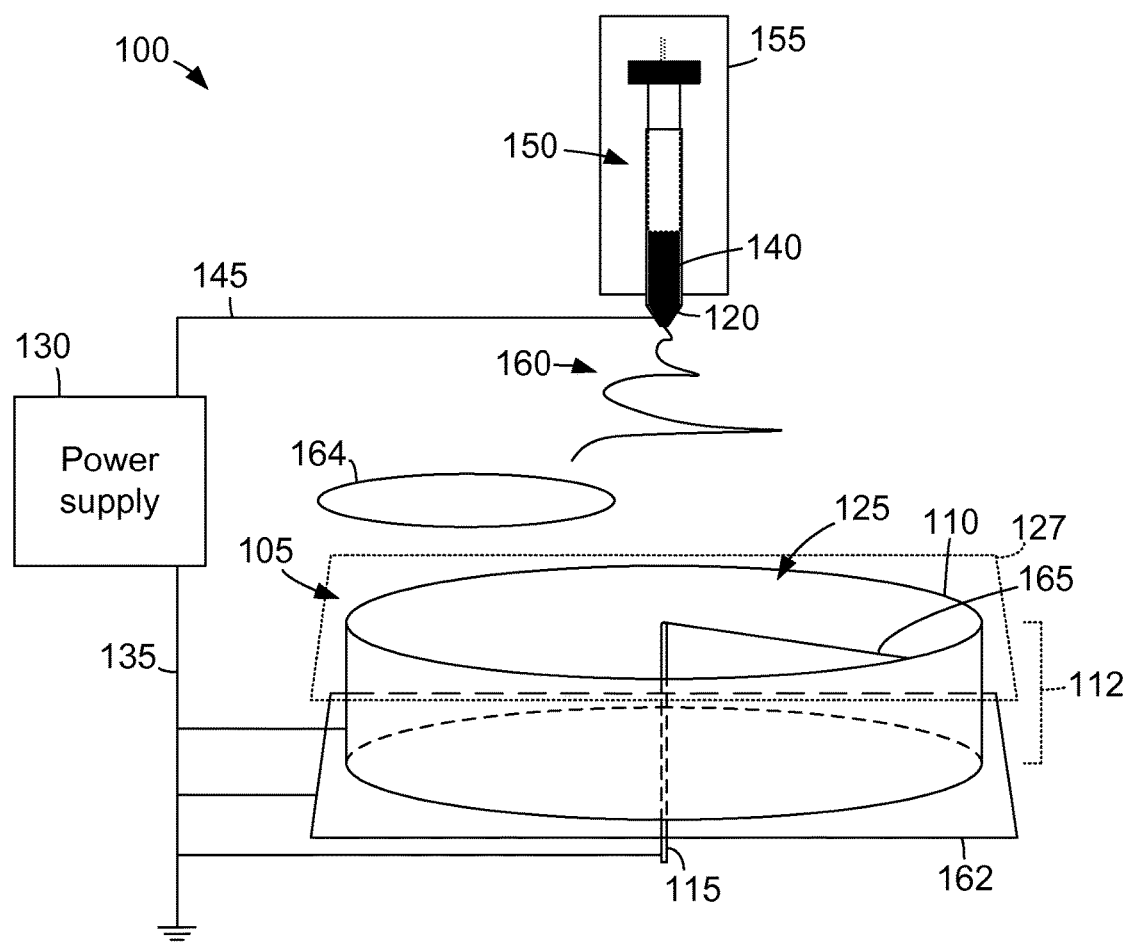
FIG. 1 is a diagram illustrating a perspective view of an example electrospinning system for producing a structure of radially aligned fibers.

Embodiments provided herein facilitate repairing biological tissue with the use of a biomedical patch including a plurality of fibers. Such fibers may have a very small cross-sectional diameter (e.g., from 1-1000 nanometers) and, accordingly, may be referred to as nanofibers. While biomedical patches are described herein with reference to dura mater and use as a dural substitute, embodiments described may be applied to any biological tissue. Moreover, although described as biomedical patches, structures with aligned fibers may be used for other purposes. Accordingly, embodiments described are not limited to biomedical patches.

In operation, biomedical patches provided herein facilitate cell growth and may be referred to as "membranes," "scaffolds," "matrices," or "substrates." Such biomedical patches further facilitate cell migration from a perimeter of the patch to a center of the biomedical patch. Biomedical patches with aligned fibers, as described herein, may promote significantly faster healing and/or regeneration of tissue such as the dura mater than substitutes lacking nanoscopic organization and directional cues.

Dura mater is a membranous connective tissue located at the outermost of the three layers of the meninges surrounding the brain and spinal cord, which covers and supports the dural sinuses and carries blood from the brain towards the heart. Dural substitutes are often needed after a neurosurgical procedure to repair, expand, or replace the incised, damaged, or resected dura mater.

Although many efforts have been made, the challenge to develop a suitable dural substitute has been met with limited success. Autografts (e.g., fascia lata, temporalis fascia, and pericranium) are preferable because they do not provoke severe inflammatory or immunologic reactions. Potential drawbacks of autografts include the difficulty in achieving a watertight closure, formation of scar tissue, insufficiently accessible graft materials to close large dural defects, increased risk of infection, donor site morbidity, and the need for an additional operative site. Allografts and xenografts are often associated with adverse effects such as graft dissolution, encapsulation, foreign body reaction, scarring, adhesion formation, and toxicity-induced side effects from immunosuppressive regimens. Lyophilized human dura mater as a dural substitute has also been reported as a source of transmittable diseases, specifically involving prions, such as Creutzfeldt-Jakob disease.

In terms of materials, non-absorbable synthetic polymers, such as silicone and expanded polytetrafluoroethylene (ePTFE), often cause serious complications that may include induction of granulation tissue formation due to their chronic stimulation of the foreign body response. Natural absorbable polymers, including collagen, fibrin, and cellulose, may present a risk of infection and disease transmission. As a result, synthetic polymers such as poly(3-hydroxybutyrate-co-3-hydroxyvalerate) (PHBV), poly(lactic acid) (PLA), polyglycolic acid (PGA), PLA-PCL-PGA ternary copolymers, and hydroxyethylmethacrylate hydrogels have recently attracted attention as biodegradable implant materials for dural repair. Methods and systems described herein may be practiced with these materials and/or any biomedical polymer.

In order to facilitate successful regeneration and/or repair of the dura mater following surgery, a synthetic dural substitute or biomedical patch should promote: i) adhesion of dural fibroblasts (the primary cell type present in the dura) to the surface of the biomedical patch; ii) migration of dural fibroblasts from the periphery of the biomedical patch toward the center; and iii) minimal immune response. To date, synthetic dural substitutes have been tested only in the form of foils, films, meshes, glues, and hydrogels. Due to the isotropic surface properties, such substitutes are not well-suited for cell attachment and directed, inward migration.

This problem can be potentially solved by fabricating the polymers as nanoscale fibers with a specific order and organization. For example, the speed of cell migration may be very low on flat, isotropic surfaces, whereas cells may migrate over a very long distance in a highly correlated fashion with constant velocity on a uniaxially aligned, fibrous scaffold.

Electrospinning is an enabling technique which can produce nanoscale fibers from a large number of polymers. The electrospun nanofibers are typically collected as a randomly-oriented, nonwoven mat. Uniaxially aligned arrays of nanofibers can also be obtained under certain conditions, specifically when employing an air-gap collector or a mandrel rotating at a high speed. However, uniaxially aligned nanofiber scaffolds promote cell migration only along one specific direction and are thus not ideally suited as dural substitutes.

In order to promote cell migration from the surrounding tissue to the center of a dural defect and shorten the time for healing and regeneration of dura mater, a surface patterned with aligned (e.g., aligned radially and/or in one or more polygons), nanoscale features would be highly advantageous as an artificial dural substitute. More specifically, scaffolds constructed with aligned nanofibers could meet such a demand by guiding and enhancing cell migration from the edge of a dural defect to the center.

Many polymers are available for use in electrospinning. In some embodiments described herein, nanofibers for dura substitutes are produced as the electrospun polymer from poly($\varepsilon$-caprolactone) (PCL), an FDA approved, semicrystalline polyester that can degrade via hydrolysis of its ester linkages under physiological conditions with nontoxic degradation products. This polymer has been extensively utilized and studied in the human body as a material for fabrication of drug delivery carriers, sutures, or adhesion barriers. As described herein, electrospun PCL nanofibers may be aligned to generate scaffolds that are useful as dural substitutes.

Embodiments provided herein facilitate producing a novel type of artificial tissue substitute including a polymeric nanofiber material, which is formed through a novel method of electrospinning. This polymeric material includes non-woven nanofibers (e.g., fibers having a diameter of 1-1000 nanometers) which are aligned within a material sheet.

In exemplary embodiments, a material with aligned nanofibers is formed through a novel method of electrospinning that employs a collector including one or more first, or "peripheral," electrodes defining an area and/or at least partially circumscribing the area, and a second, or "inner," electrode positioned within the area. When the electrodes are electrically charged at a first polarity, and a spinneret dispensing a polymer (e.g., toward the inner electrode) is electrically charged at a second polarity opposite the first polarity, the dispensed polymer forms a plurality of fibers extending from the inner electrode to the peripheral electrode(s). Electrodes may include a rounded (e.g., convex) surface, such that a depression, or "well", is formed in the electrode-facing side of a structure of fibers. Alternatively, electrodes may include a concave surface, such that a well is formed in the side of the structure facing away from the electrodes.

In some embodiments, the collector includes a single inner electrode and a single peripheral electrode. In other embodiments, the collector includes a plurality of peripheral electrodes, and the dispensed polymer may form fibers extending between such peripheral electrodes in addition to fibers extending from the inner electrode to one or more of the peripheral electrodes.

Further, in some embodiments, multiple areas are defined and/or partially circumscribed by peripheral electrodes. For example, an inner peripheral electrode may define an inner enclosed area surrounding the inner electrode, and an outer peripheral electrode may define an outer enclosed area surrounding the inner peripheral electrode. In other embodiments, electrodes are arranged in an array, such as a grid and/or other polygonal pattern (e.g., a hexagonal pattern), and multiple, partially overlapping areas may be defined by such electrodes. For example, an inner electrode of one area may function as a peripheral electrode of another area. In such embodiments, the dispensed polymer may form fibers extending between the electrodes of the collector, such that the fibers define the sides of a plurality of polygons, with the electrodes positioned at the vertices of the polygons.

Unlike known nanofiber structures, aligned nanofiber materials provided herein are capable of presenting nanoscale topographical cues to local cells that enhance and direct cell migration (e.g., throughout the material sheet or into the center of the material sheet). As a result, aligned nanofiber materials may induce faster cellular migration and population than randomly oriented materials, such as processed gold-standard collagen matrices. Materials described herein may be particularly useful as a substrate for various types of biomedical patches or grafts designed to induce wound protection, closure, healing, repair, and/or tissue regeneration.

A scaffold of aligned nanofibers, as described herein, possesses significant potential as an artificial dural substitute, in that it is capable of encouraging robust cell migration from apposed intact dura and promoting rapid cellular population of the nanofiber matrix required to induce dural repair. In addition, such nanofiber materials offer the advantage of being inexpensive to produce, fully customizable, and resorbable. Nanofiber dural substitutes may also reduce the risk of contractures and fully eliminate the risk of transmitted zoonotic disease when applied intraoperatively, generally improving patient outcomes following surgery.

Inner Electrode and Peripheral Electrode(s)

FIG. 1 is a diagram illustrating a perspective view of an exemplary electrospinning system 100 for producing a structure of radially aligned fibers. System 100 includes a collector 105 with a first electrode 110, which may be referred to as a peripheral electrode, and a second electrode 115, which may be referred to as an inner electrode or central electrode. System 100 also includes a spinneret 120. Peripheral electrode 110 defines an enclosed area 125, and central electrode 115 is positioned approximately at a center of enclosed area 125.

System 100 is configured to create an electric potential between collector 105 and spinneret 120. In one embodiment, peripheral electrode 110 and central electrode 115 are configured to be electrically charged at a first amplitude and/or polarity. For example, peripheral electrode 110 and central electrode 115 may be electrically coupled to a power supply 130 via a conductor 135. Power supply 130 is configured to charge peripheral electrode 110 and central electrode 115 at the first amplitude and/or polarity via conductor 135.

In the embodiment illustrated in FIG. 1, peripheral electrode 110 is a ring defining an enclosed area 125 which is circular. For example, circular enclosed area 125 may have a diameter of between 1 centimeter and 20 centimeters. In other embodiments, peripheral electrode 110 may be any shape suitable for use with the methods described herein. For example, peripheral electrode 110 may define an elliptical, ovular, rectangular, square, triangular, and/or other rectilinear or curvilinear enclosed area 125. In some embodiments, peripheral electrode 110 defines an enclosed area 125 of between 5 square centimeters and 100 square centimeters. Peripheral electrode 110 may have a height 112 of between 0.5 and 2.0 centimeters. Central electrode 115 may include a metallic needle and/or any other structure terminating in a point or set of points.

In one embodiment, enclosed area 125 defines a horizontal plane 127. Spinneret 120 is aligned with central electrode 115 and vertically offset from horizontal plane 127 at a variable distance. For example, spinneret 120 may be vertically offset from horizontal plane 127 at a distance of 1 centimeter to 100 centimeters.

Spinneret 120 is configured to dispense a polymer 140 while electrically charged at a second amplitude and/or polarity opposite the first polarity. As shown in FIG. 1, spinneret 120 is electrically coupled to power supply 130 by a conductor 145. Power supply 130 is configured to charge spinneret 120 at the second amplitude and/or polarity via conductor 145. In some embodiments, power supply 130 provides a direct current (DC) voltage (e.g., between 10 kilovolts and 17 kilovolts). In one embodiment, conductor 145 is charged positively, and conductor 135 is charged negatively or grounded. In some embodiments, power supply 130 is configured to allow adjustment of a current, a voltage, and/or a power.

In one embodiment, spinneret 120 is coupled to a syringe 150 containing polymer 140 in a liquid solution form. Syringe 150 may be operated manually or by a syringe pump 155. In an exemplary embodiment, spinneret 120 is a metallic needle having an aperture between 100 micrometers and 2 millimeters in diameter.

As syringe 150 pressurizes polymer 140, spinneret 120 dispenses polymer 140 as a stream 160. Stream 160 has a diameter approximately equal to the aperture diameter of spinneret 120. Stream 160 descends toward collector 105. For example, stream 160 may fall downward under the influence of gravity and/or may be attracted downward by a charged conductive surface 162 positioned below collector 105. For example, conductive surface 162 may be electrically coupled to conductor 135 and charged at the same amplitude and/or polarity as peripheral electrode 110 and central electrode 115. As stream 160 descends, polymer 140 forms one or more solid polymeric fibers 165.

In some embodiments, a mask 164 composed of a conducting or non-conducting material is applied to collector 105 to manipulate deposition of fibers 165. For example, mask 164 may be positioned between spinneret 120 and collector 105 such that no fibers 165 are deposited on collector 105 beneath mask 164. Moreover, mask 164 may be used as a time-variant mask by adjusting its position while spinneret 120 dispenses polymer 140, facilitating spatial variation of fiber density on collector 105. While mask 164 is shown as circular, mask 164 may have any shape (e.g., rectangular or semi-circular) and size suitable for use with system 100. Alternatively, or in addition, deposition of fibers 165 on collector 105 may be manipulated by adjusting the position of collector 105 with respect to spinneret 120 or by spatially varying the electrical potential applied between the spinneret 120 and/or the electrodes making up the collector 105. For example, positioning one side of collector 105 directly beneath spinneret 120 may cause more fibers 165 to be deposited on that side than are deposited on the opposite side of collector 105.

Figure 2:
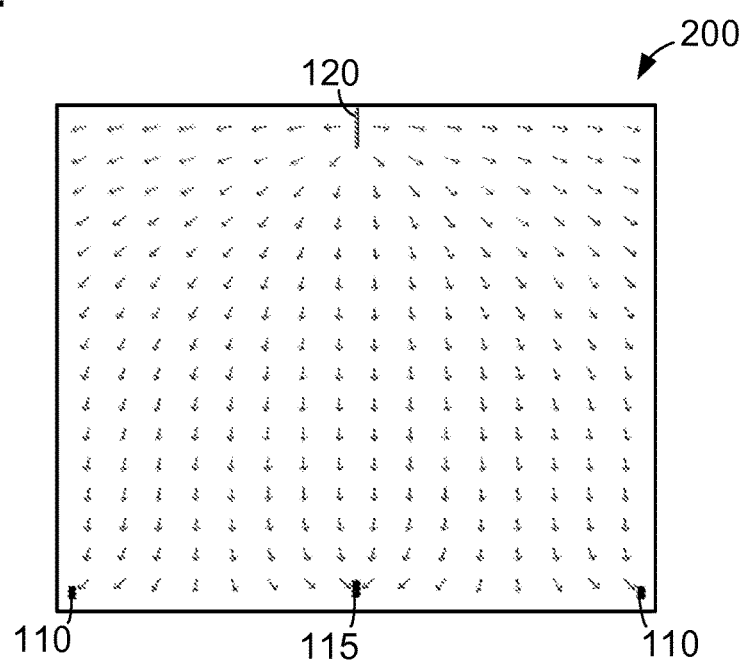
FIG. 2 is a diagram illustrating an electric field generated by the electrospinning system shown in FIG. 1.

FIG. 2 is a diagram 200 illustrating an electric field generated by system 100. Diagram 200 shows a two dimensional, cross-sectional view of electric field strength vectors between spinneret 120 and peripheral electrode 110 and central electrode 115 of collector 105 (shown in FIG. 1). Unlike known electrospinning systems, the electric field vectors (stream lines) in the vicinity of the collector are split into two populations, pointing toward the peripheral electrode 110 and pointing toward the central electrode 115.

Neglecting the effect of charges on the polymeric fibers, the electrical potential field can be calculated using the Poisson equation, $$\nabla^2 V = \frac{-\rho}{\varepsilon},$$

where V is the electrical potential, ε is the electrical permittivity of air, and ρ is the spatial charge density. The electrical field, E, can then be calculated by taking the negative gradient of the electrical potential field, $E = -\nabla V$. Here, the electrical field was calculated to verify the alignment effect demonstrated by deposited fibers, which was performed using the software COMSOL3.3.

Figure 3:
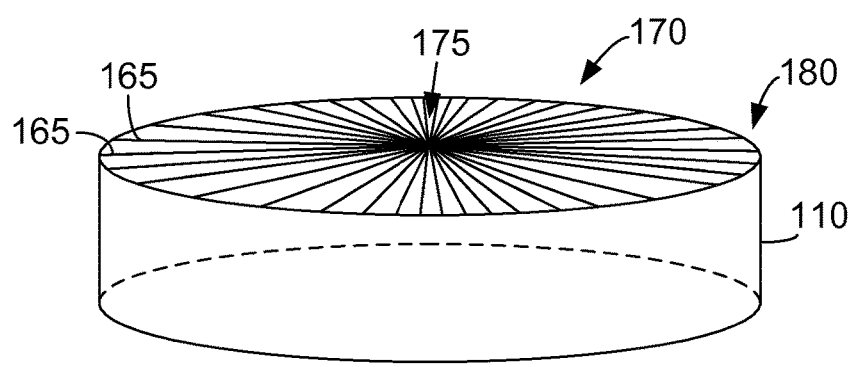
FIG. 3 is a diagram of an electrode removed from the electrospinning system shown in FIG. 1 and having a plurality of fibers deposited thereon forming a biomedical patch.

FIG. 3 is a diagram of peripheral electrode 110 removed from electrospinning system 100 (shown in FIG. 1) and having a plurality of fibers 165 deposited thereon forming a biomedical patch 170. Fibers 165 extend radially between a center 175 corresponding to the position of central electrode 115 (shown in FIG. 1) and a perimeter 178 corresponding to the position of peripheral electrode 110. For example, perimeter 178 may be a circular perimeter about center 175 defining a diameter of between 1 centimeter and 6 centimeters.

Biomedical patch 170 is illustrated with a small quantity of fibers 165 in FIG. 3 for clarity. In some embodiments, biomedical patch 170 includes thousands, tens of thousands, hundreds of thousands, or more fibers 165, evenly distributed throughout enclosed area 125 (shown in FIG. 1) of peripheral electrode 110. Even with millions of fibers 165, biomedical patch 170 is flexible and/or pliable, facilitating application of biomedical patch 170 to uneven biological tissue surfaces, such as the surface of the dura mater.

The radial alignment of fibers 165 demonstrates the shortest possible path between perimeter 178 and center 175. Accordingly, biomedical patch 170 also facilitates cell migration directly from perimeter 178 to center 175, enabling a reduction in time required for cells to infiltrate and populate applied biomedical patch, and for native tissue to regenerate.

Fibers 165 have a diameter of 1-1000 nanometers. In one embodiment, fibers have a diameter of approximately 220 nanometers (e.g., 215 nm to 225 nm). The diameter of the fibers 165, thickness of the biomedical patch 170, and/or fiber density within the biomedical patch 170 may affect the durability (e.g., tensile strength) of biomedical patch 170. Biomedical patch 170 may be produced with various mechanical properties by varying the thickness and/or the fiber density of the biomedical patch 170 by operating electrospinning system 100 for relatively longer or shorter durations.

Figure 4:
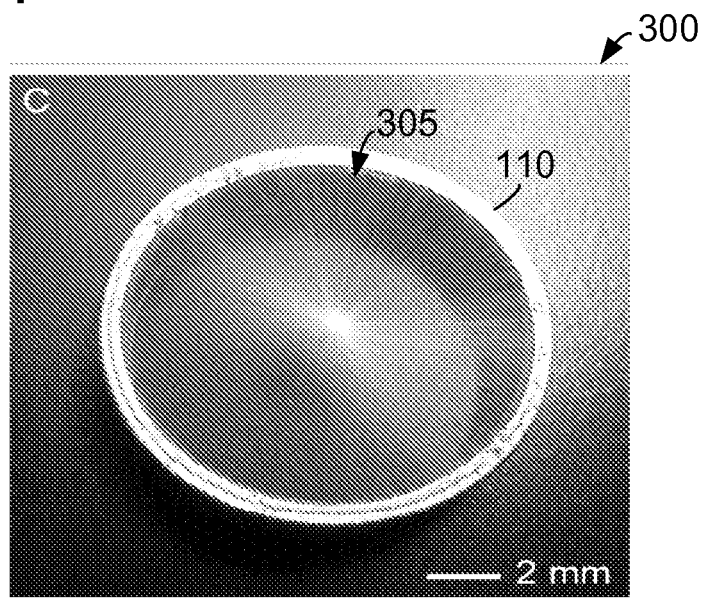
FIG. 4 is a photograph of a biomedical patch including a plurality of radially aligned electrospun fibers deposited on a peripheral electrode.
Figure 5:
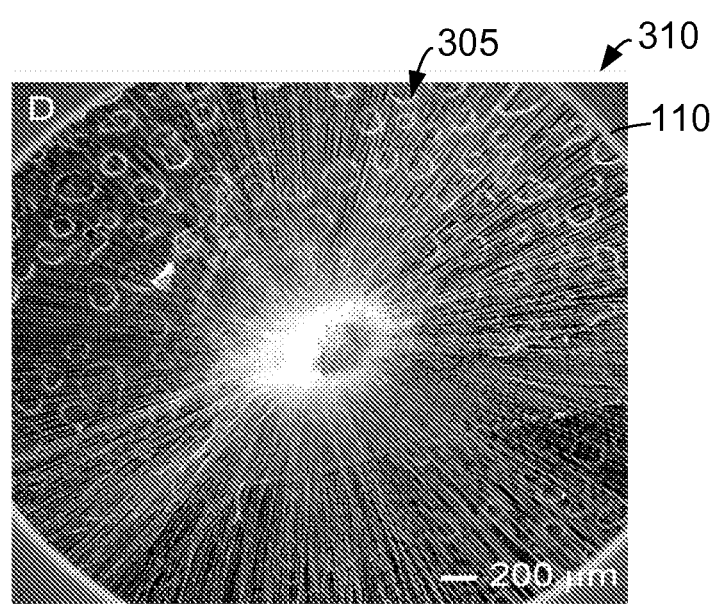
FIG. 5 is a scanning electron microscope (SEM) image of the biomedical patch shown in FIG. 4, further illustrating that the fibers of the biomedical patch are radially aligned.

FIG. 4 is a photograph 300 of a biomedical patch 305 including a plurality of radially aligned electrospun fibers deposited on a peripheral electrode 110. FIG. 5 is a scanning electron microscope (SEM) image 310 of biomedical patch 305, further illustrating that the fibers of biomedical patch 305 are radially aligned.

Figure 6:
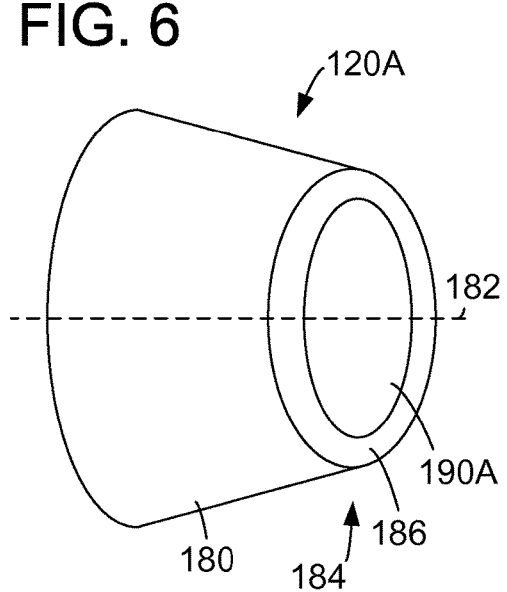
FIG. 6 is an illustration of a solid fiber spinneret.

Referring to FIGS. 1 and 3, fibers 165 may be solid or hollow. In some embodiments, the size and/or structure of fibers 165 is determined by the design of spinneret 120. FIG. 6 is an illustration of a solid fiber spinneret 120A. Solid fiber spinneret 120A includes a conical body 180 defining a center line 182. At a dispensing end 184, conical body 180 includes an annulus 186. Annulus 186 defines a circular aperture 190A, through which polymer 140 may be dispensed. Fibers 165 produced with solid fiber spinneret 120A have a solid composition.

Figure 7:
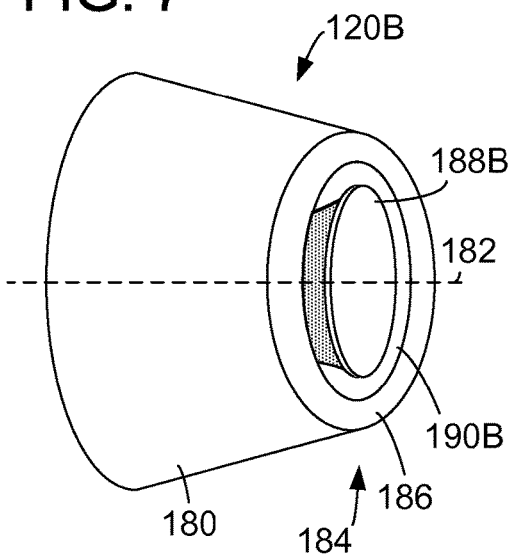
FIG. 7 is an illustration of a hollow fiber spinneret.

FIG. 7 is an illustration of a hollow fiber spinneret 120B. Like solid fiber spinneret 120A, hollow fiber spinneret 120B includes a conical body 180 with an annulus 186 at a dispensing end 184. Hollow fiber spinneret 120B also includes a central body 188B positioned within annulus 186. Annulus 186 and central body 188B define an annular aperture 190B. Accordingly, when polymer 140 is dispensed by hollow fiber spinneret 120B, fibers 165 have a hollow composition, with an exterior wall surrounding a cavity. The exterior wall of a fiber 165 dispensed by hollow fiber spinneret 120B defines an outer diameter corresponding to the inner diameter of annulus 186 and an inner diameter corresponding to the diameter of central body 188B. Accordingly, the outer diameter and inner diameter of hollow fibers 165 may be adjusted by adjusting the diameters of annulus 186 and central body 188B.

Hollow fiber spinneret 120B facilitates incorporating a substance, such as a biological agent, growth factor, and/or a drug (e.g., a chemotherapeutic substance), into biomedical patch 170. For example, the substance may be deposited within a cavity defined by hollow fibers 165 of biomedical patch 170. In one embodiment, polymer 140 is selected to create porous and/or semi-soluble fibers 165, and the substance is dispensed from the cavity through fibers 165. In another embodiment, polymer 140 is degradable, and the substance is dispensed as fibers 165 degrade in vivo. For example, fibers 165 may be configured to degrade within 12 months, 6 months, or 3 months. The degradation rate of polymer 140 may be manipulated by adjusting a ratio of constituent polymers within polymer 140.

In another embodiment, a substance is delivered by solid fibers 165. For example, a solid fiber 165 may be created from a polymer 140 including the substance in solution. As solid fiber 165 degrades, the substance is released into the surrounding tissue.

As shown in FIGS. 6 and 7, annulus 186 is perpendicular to center line 182. In an alternative embodiment, annulus 186 is oblique (e.g., oriented at an acute or obtuse angle) with respect to center line 182. The outside diameter of fibers 165 may be determined by the inside diameter of annulus 186.

Some embodiments facilitate producing a biomedical patch having radially aligned fibers and non-radially aligned fibers. For example, radially aligned fibers may be deposited into a first layer, and non-radially aligned fibers may be deposited into a second layer. Alternatively, radially aligned non-radially aligned fibers may be deposited into a single layer (e.g., simultaneously, sequentially, and/or alternately). Referring to FIG. 1, system 100 may be used to create randomly oriented fibers by charging or grounding conductive surface 162. Optionally, peripheral electrode 110 and central electrode 115 may be uncharged or ungrounded (e.g., decoupled from conductor 135).

Figure 8:
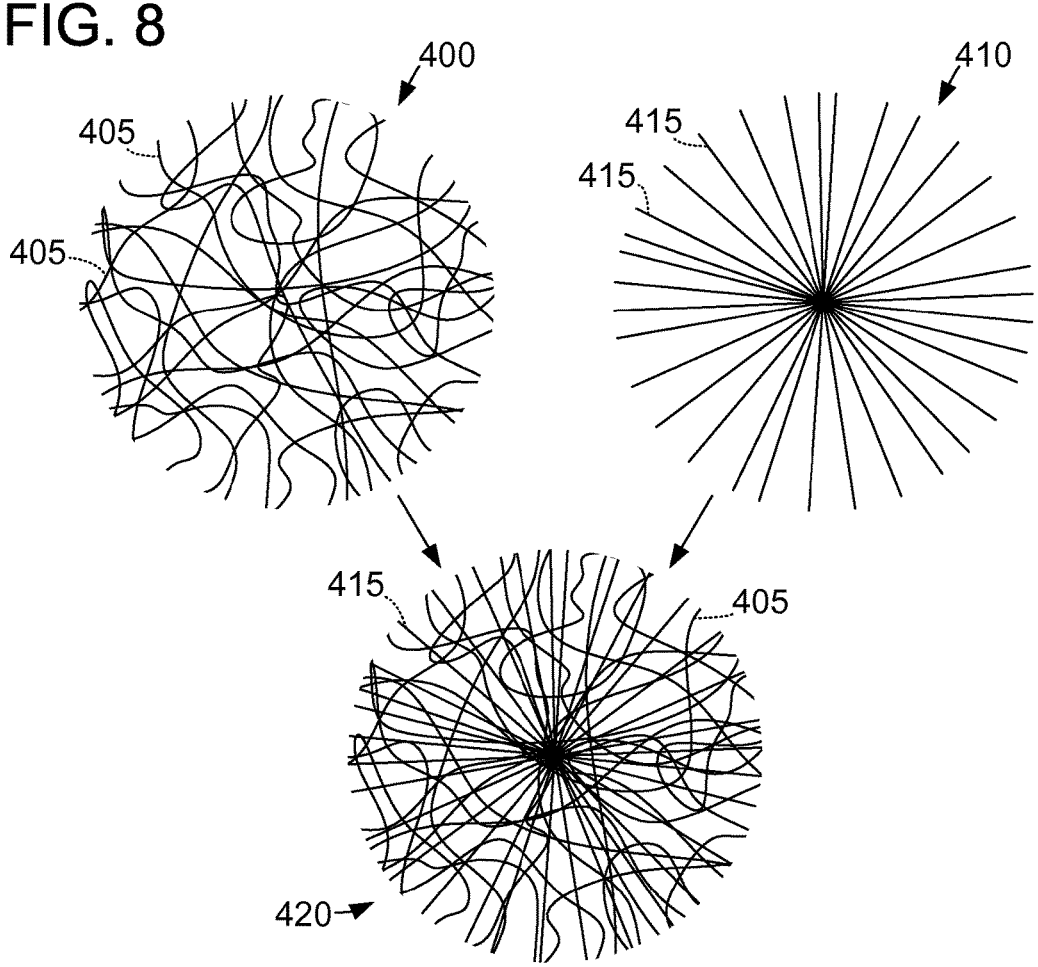
FIG. 8 is an illustration of a biomedical patch layer with a plurality of randomly oriented fibers, a biomedical patch layer with a plurality of radially aligned fibers, and a multi-layer biomedical patch including multiple orders of fibers.

FIG. 8 is an illustration of a biomedical patch layer 400 with a plurality of randomly oriented fibers 405 and a biomedical patch layer 410 with a plurality of radially aligned fibers 415. As shown in FIG. 8, biomedical patch layers 400 and 410 may be combined (e.g., overlaid) to produce a multi-layer biomedical patch 420 with both randomly oriented fibers 405 and radially aligned fibers 415, or any other combination of any number or type of fiber layers. Combining non-radially aligned fibers 405 and radially aligned fibers 415 facilitates providing a biomedical patch that promotes cell migration to a center of the biomedical patch while exhibiting potentially greater durability (e.g., tensile strength) than a biomedical patch having only radially aligned fibers 415. Combining non-radially aligned fibers 405 and radially aligned fibers 415 may also enable spatial control of cell migration and infiltration along an axis perpendicular to the plane of the biomedical patch, facilitating the formation and organization of specific layers of cells and/or extracellular matrix proteins resembling natural tissue strata.

In some embodiments, multiple biomedical patch layers 410 with radially aligned fibers 415 may be combined to create a multi-layer biomedical patch. For example, referring to FIGS. 1 and 3, after depositing a first set of fibers on collector 105, one may wait for the first set of fibers 165 to solidify completely or cure and then deposit a second set of fibers 165 on collector 105. The second set of fibers 165 may be deposited directly over the first set of fibers 165 on collector 105. Alternatively, the first set of fibers 165 may be removed from collector 105, and the second set of fibers 165 may be deposited on conductive surface 162 and/or collector 105 and then removed and overlaid on the first set of fibers 165. Such embodiments facilitate increased durability of the biomedical patch, and added spatial control of cell migration/activity, even where only radially aligned fibers are used. In some embodiments, a hydrogel or polymeric scaffold may be disposed between biomedical patch layers 400 and/or biomedical patch layers 410.

A multi-layered biomedical patch may be useful for dural grafts as well as other tissue engineering applications. Sequential layers of fibers can be created with varying orders (e.g., radially aligned or randomly oriented) and densities (e.g., low or high fiber density), which may allow specific types of cells to infiltrate and populate select layers of the artificial biomedical patch. For example, biomedical patches containing a high fiber density generally prohibit cellular migration and infiltration, while biomedical patches containing a low fiber density generally enhance cellular migration and infiltration.

Overall, the ability to form multi-layered fiber materials, as described herein, may be extremely beneficial in the construction of biomedical patches designed to recapitulate the natural multi-laminar structure of not only dura mater, but also other biological tissues such as skin, heart valve leaflets, pericardium, and/or any other biological tissue. Furthermore, one or more layers of a biomedical patch may be fabricated from biodegradable polymers such that the resulting nanofiber materials fully resorb following implantation. Manipulation of the chemical composition of the polymers utilized to fabricate these scaffolds may further allow for specific control of the rate of degradation and/or resorption of a biomedical patch following implantation.

Figure 9:
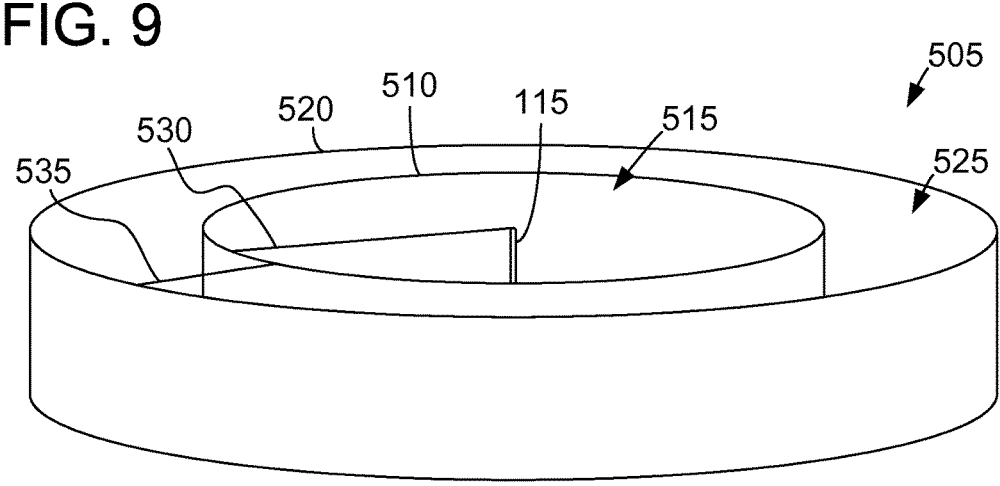
FIG. 9 is a diagram of a collector with a central electrode, an inner peripheral electrode defining an inner enclosed area, and an outer peripheral electrode defining an outer enclosed area.

Some embodiments provide a biomedical patch including a plurality of nested (e.g., concentric) areas. FIG. 9 is a diagram of a collector 505 with a central electrode 115, a first or inner peripheral electrode 510 defining a first or inner enclosed area 515, and a second or outer peripheral electrode 520 defining a second or outer enclosed area 525 that is larger than the inner enclosed area 515. In some embodiments, outer peripheral electrode 520 is concentrically oriented with inner peripheral electrode 510. While inner peripheral electrode 510 and outer peripheral electrode 520 are shown as defining circular enclosed areas 515, 525 in FIG. 9, inner peripheral electrode 510 and outer peripheral electrode 520 may define enclosed areas 515, 525 of any shape suitable for use with the methods described herein. Moreover, inner enclosed area 515 and outer enclosed area 525 may have different shapes and/or different centers.

In operation with electrospinning system 100 (shown in FIG. 1), central electrode 115 and inner peripheral collector 505 are charged at the first amplitude and/or polarity (opposite the polarity at which spinneret 120 is charged) while spinneret 120 dispenses polymer 140 as stream 160. Stream 160 descends toward collector 505 and forms one or more fibers 530 extending from central electrode 115 to inner peripheral electrode 510.

Figure 10:
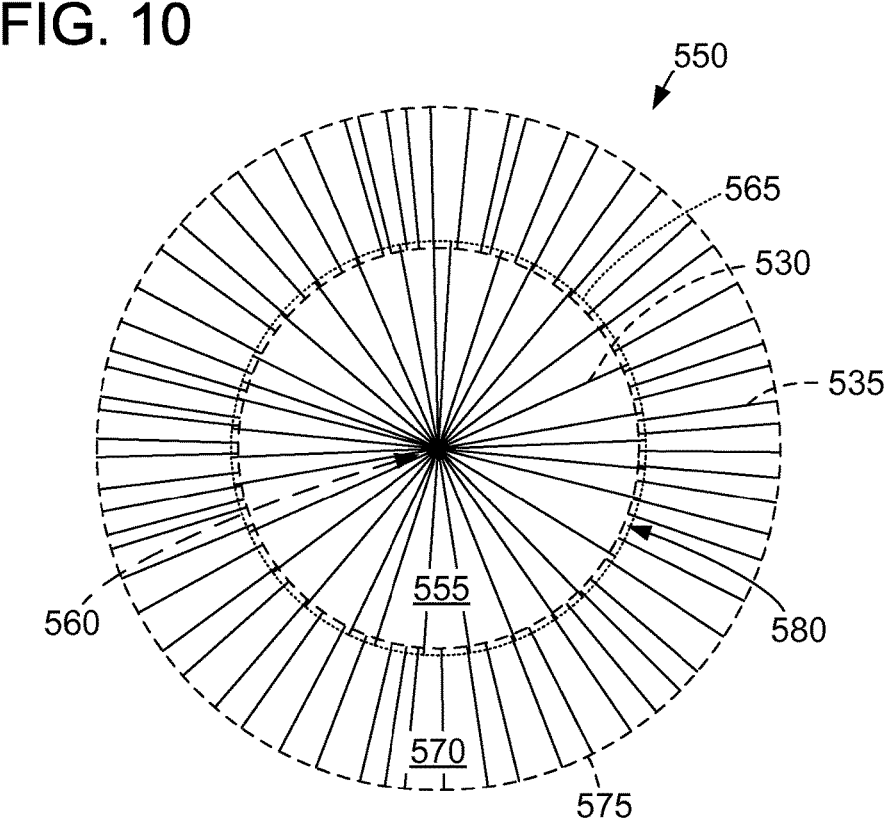
FIG. 10 is a diagram of a concentric biomedical patch that may be produced utilizing the collector shown in FIG. 9 in conjunction with the electrospinning system shown in FIG. 1.

The charge of the first polarity is removed from central electrode 115 (e.g., by decoupling central electrode 115 from conductor 135), and outer peripheral electrode 520 is charged at the first amplitude and/or polarity. Spinneret 120 dispenses polymer 140 as stream 160, which descends toward collector 505 and forms one or more fibers 535 extending from inner peripheral electrode 510 to outer peripheral electrode 520. Together, fibers 530 and 535 form a concentric biomedical patch 550, as shown in FIG. 10. In some embodiments, the charge is not removed from central electrode 115 prior to depositing fibers 535 between inner peripheral electrode 510 and outer peripheral electrode 520.

FIG. 10 is a diagram of a concentric biomedical patch 550 that may be produced with collector 505 (shown in FIG. 9). Fibers 530 define an inner area 555, shown as a circle extending from a center 560 to an inner perimeter 565. An outer area 570 includes fibers 535 extending approximately from inner perimeter 565 (e.g., about 100 µm to 2000 µm inside inner perimeter 565) to an outer perimeter 575. Fibers 535 are oriented radially or approximately (e.g., within 1, 3, or 5 degrees) radially with respect to center 560.

As shown in FIG. 10, inner area 555 and outer area 570 may overlap in an overlapping area 580. In one embodiment, overlapping area 580 corresponds to a thickness of inner peripheral ring 510 (shown in FIG. 8). Similar to FIG. 3, concentric biomedical patch 550 is shown in FIG. 10 with a small quantity of fibers 530 and 535 for clarity. In some embodiments, inner area 555 and outer area 570 each include thousands, tens of thousands, hundreds of thousands, or more fibers 530 and 535, respectively. Fibers 530 and fibers 535 may be coupled to each other in overlapping area 580. For example, fibers 535 may be deposited before fibers 530 have completely solidified (or vice versa). In some embodiments, fibers 530 and fibers 535 are deposited on collector 505 (shown in FIG. 9) simultaneously or in an alternating manner.

Embodiments such as those shown in FIGS. 9 and 10 facilitate providing a biomedical patch having a relatively consistent fiber density throughout. For contrast, if fibers 530 extended from center 560 to outer perimeter 575, the fiber density at center 560 would be considerably higher than the fiber density at outer perimeter 575. Low peripheral fiber density may compromise durability of a biomedical patch near an outer perimeter, especially at large diameters (e.g., above 5 or 6 centimeters). Accordingly, such embodiments further facilitate providing a biomedical patch of large diameter (e.g., up to 10 or 12 centimeters) while maintaining durability of the biomedical patch. In some embodiments, a layer of non-radially aligned fibers is combined with biomedical patch 550, as described above with regard to FIG. 8, which may further enhance durability of biomedical patch 550.

In some embodiments, the spatial fiber density within inner area 555 is different from the spatial fiber density within outer area 570. In one example, fibers 530 are deposited between central electrode 115 and inner peripheral electrode 510 for a first duration, and fibers 535 are deposited between inner peripheral electrode 510 and outer peripheral electrode 520 for a second duration.

While collector 505 and concentric biomedical patch 550 are illustrated with circular inner and outer areas, any quantity and shape of peripheral electrodes may be used to create any number of distinct fiber areas within a biomedical patch.

Figure 11:
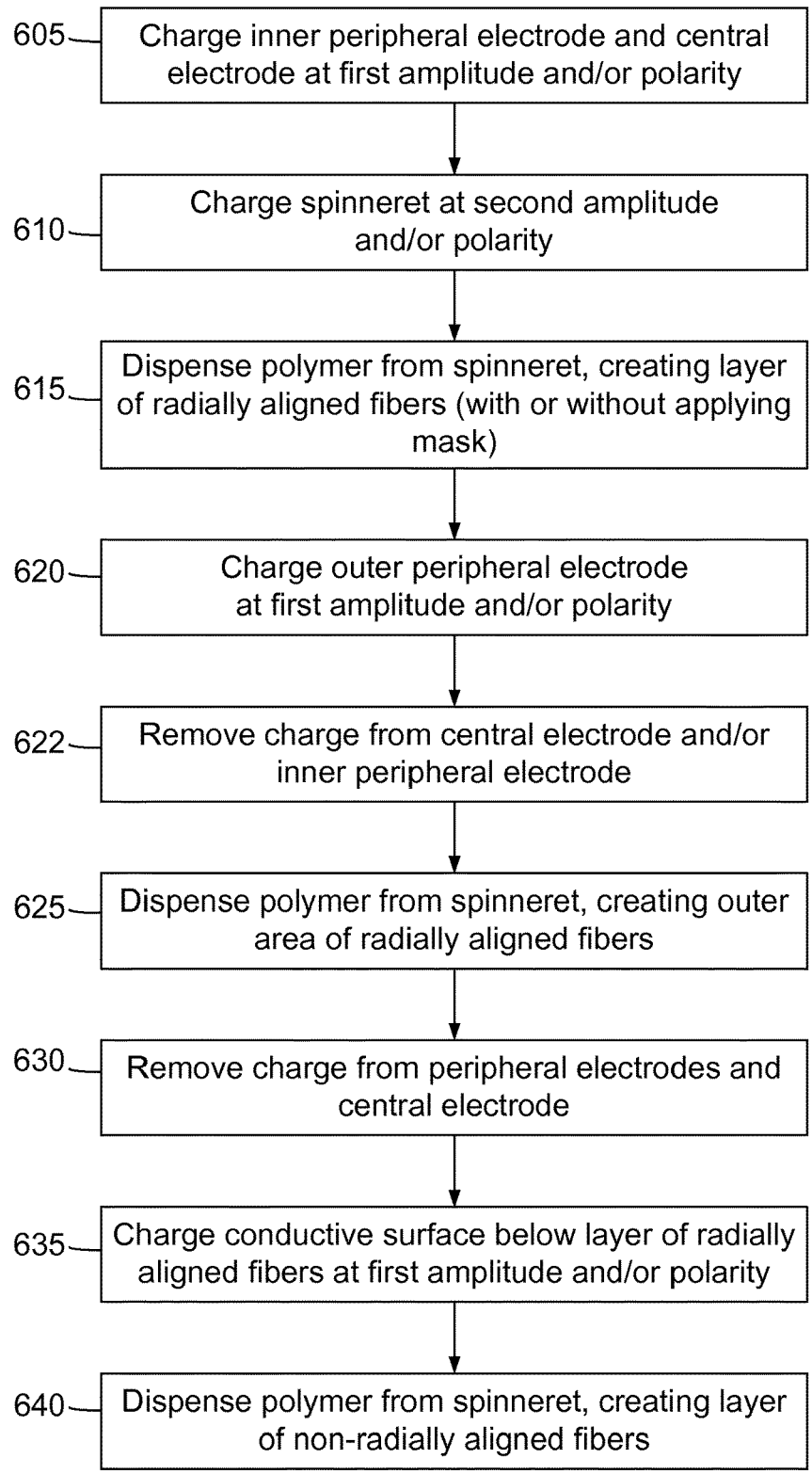
FIG. 11 is a flowchart of an exemplary method for producing a structure of radially aligned fibers using a peripheral electrode defining an enclosed area and a central electrode positioned approximately at a center of the enclosed area.

FIG. 11 is a flowchart of an exemplary method 600 for producing a structure of radially aligned fibers using a peripheral electrode defining an enclosed area and a central electrode positioned approximately at a center of the enclosed area. While one embodiment of method 600 is shown in FIG. 11, it is contemplated that any of the operations illustrated may be omitted and that the operations may be performed in a different order than is shown.

Method 600 includes electrically charging 605 the peripheral electrode and the central electrode at a first amplitude and/or polarity (e.g., negatively charging or grounding). A spinneret approximately aligned with the central electrode is electrically charged 610 at a second amplitude and/or polarity opposite the first amplitude and/or polarity (e.g., positively charged).

A polymer (e.g., a liquid polymer) is dispensed 615 from the spinneret. In an exemplary embodiment, dispensing 615 the polymer forms a plurality of polymeric fibers extending from the central electrode to the peripheral electrode to create a layer of radially aligned fibers.

Some embodiments facilitate creating a concentric structure of radially aligned fibers using multiple peripheral electrodes. In one embodiment, the peripheral electrode is an inner peripheral electrode. An outer peripheral electrode defining an outer enclosed area larger than the inner enclosed area is electrically charged 620 at the first amplitude and/or polarity. The electrical charge may or may not be removed 622 from the central electrode and/or the inner peripheral electrode. The polymer is dispensed 625 from the spinneret to create an outer area of radially aligned fibers extending from the inner peripheral electrode to the outer peripheral electrode.

Furthermore, some embodiments facilitate creating a multi-layered structure including both radially aligned fibers and non-radially aligned fibers. The electrical charge is removed 630 from the peripheral electrode(s) and the central electrode. A conductive surface below the layer of radially aligned fibers is electrically charged 635 at the first amplitude and/or polarity. The polymer is dispensed 640 from the spinneret to create a layer of non-radially aligned (e.g., randomly oriented and/or uniaxially aligned) fibers over the layer of radially aligned fibers.

Figure 12:
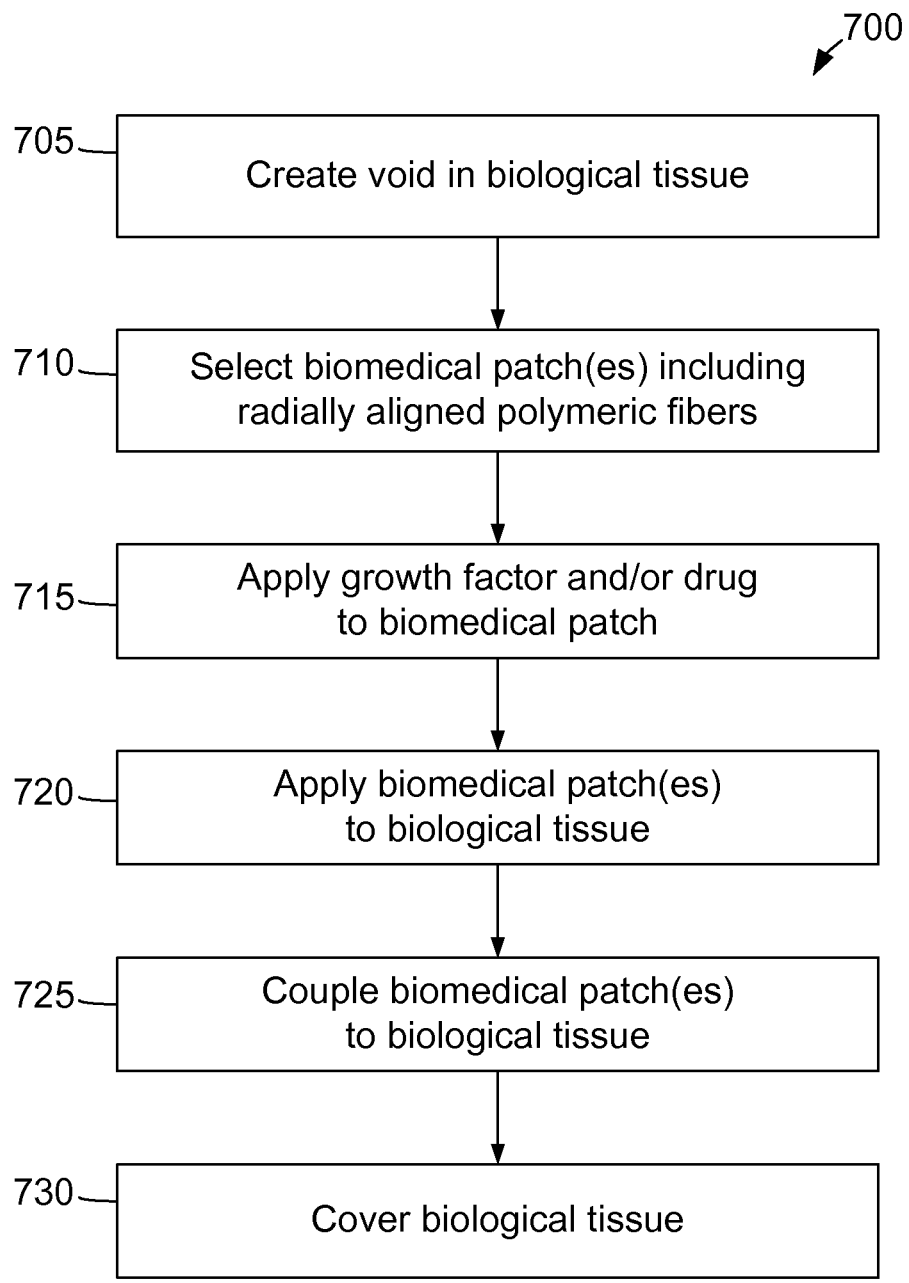
FIG. 12 is a flowchart of an exemplary method for repairing a defect, insult, or void in a biological tissue.

FIG. 12 is a flowchart of an exemplary method 700 for repairing a defect in a biological tissue. The defect may include a void, an insult, and/or any other condition resulting in diminished function of the biological tissue. In one embodiment, method 700 includes creating 705 a void in the biological tissue, and the defect is the created void. For example, the void may be created 705 by surgical incision to provide access to an underlying tissue (e.g., a tumor). In another example, the void is created 705 by excising necrotic tissue (e.g., skin cells). One or more biomedical patches capable of covering the defect are selected 710. For example, a plurality of biomedical patches may be selected 710 for a large and/or complex (e.g., irregularly shaped) defect. The biomedical patch includes a plurality of radially aligned polymeric fibers extending from a center of the biomedical patch to a perimeter of the biomedical patch. For example, a biomedical patch having a diameter greater than the diameter of an approximately circular defect may be selected 710.

The biomedical patch selected 710 may also include non-radially aligned (e.g., randomly oriented and/or uniaxially aligned) polymeric fibers. For example, radially aligned fibers and non-radially aligned fibers may be arranged in separate layers.

In some embodiments, the biomedical patch includes multiple areas of radially aligned fibers. In one embodiment, a first set of radially aligned fibers extends from a center of the biomedical patch to a first perimeter and define an inner area. A second set of radially aligned fibers extends from the first perimeter to a second perimeter and defines an outer area.

A substance such as a growth factor and/or a drug (e.g., a chemotherapeutic drug) may be applied 715 to the biomedical patch. For example, the biomedical patch may be immersed in the substance to allow the substance to occupy a cavity within hollow fibers of the biomedical patch, dope the polymer comprising the fibers in the biomedical patch, or coat the surface of the fibers within the biomedical patch.

The biomedical patch is applied 720 to (e.g., overlaid on) the biological tissue to cover at least a portion of the defect. For example, the biomedical patch may be applied 720 to dura mater tissue, cardiac tissue, and/or any biological tissue including a defect. In one embodiment, the perimeter of the biomedical patch extends past the perimeter of the defect, such that the entire defect is covered by the biomedical patch. In some embodiments, the biomedical patch is coupled 725 to the biological tissue with a plurality of sutures, adhesive, and/or any other means of attaching the biomedical patch to the biological tissue. In an alternative embodiment, the biomedical patch is simply allowed to fuse to the biological tissue, such as by adhesion of biological cells to the biomedical patch.

After the biomedical patch is applied 720 and, optionally, coupled 725, to the biological tissue, the biological tissue is covered 730. In one embodiment, other tissue overlaying the defect (e.g., dermis and/or epidermis) is repaired (e.g., sutured closed). In another embodiment, one or more protective layers are applied over the biological tissue. For example, a bandage may be applied to a skin graft, with or without a protective substance, such as a gel, an ointment, and/or an antibacterial agent. In one embodiment, the protective layer includes a nanofiber structure, such as an additional biomedical patch, as described herein.

Embodiments described herein are operable with any neurosurgical procedure involving the repair, replacement, or expansion of the dura mater, including, but not limited to, a transphenoidal procedure (e.g., surgical removal of pituitary adenomas), various types of skull base surgeries, and/or surgical removal of cranial or spinal tumors (e.g., meningiomas and/or astrocytomas). In one embodiment, a biomedical patch may be applied to a bone fracture (e.g., a complex fracture). In another embodiment, a biomedical patch may be applied to a defect in the skin (e.g. a burn).

Moreover, such embodiments are operable to provide a dura mater substitute, a biomedical patch for a skin graft (e.g., dermal or epidermal), a biomedical patch for tracheal repair, a scaffold for an artificial heart valve leaflet, an artificial mesh for surgical repair of a gastrointestinal tract (e.g., an abdominal hernia or an ulcer), an artificial mesh for surgical repair of cardiac defects. For example, a cardiac biomedical patch including radially aligned fibers may be used to promote cardiomyocyte regeneration. Embodiments described herein facilitate providing a cardiac patch of sufficient flexibility to enable movement of the biomedical patch by a biological tissue (e.g., cardiomyocytes).

In some embodiments, a biomedical patch has a thickness less than a thickness of the biological tissue being repaired. As cells migrate along the radial fibers of the biomedical patch, the biological tissue is regenerated.

Biomedical patches with radially aligned polymeric fibers facilitate reducing the expense of tissue repair, improving tissue healing time, and reducing or eliminating the risk of zoonotic infection. Moreover, such biomedical patches are relatively simple to manufacture, enabling customization of shape, size, and chemical composition and improved availability and non-immunogenicity. In addition, biomedical patches with radially aligned polymeric fibers exhibit excellent handling properties due to their cloth-like composition, eliminate the need for a second surgery to harvest autologous graft tissue, and reduce the risk of contracture and adhesion when compared with known products.

Experimental Results

Dura mater is a complex, fibrous membrane that consists of numerous cells and cell types, extracellular matrix proteins, and trophic factors, all of which play an important role in the colonization and duralization of artificial dural substitutes, and the successful implementation of such biomedical patches in vivo. In order to evaluate the capability of radially aligned nanofibers to interface with natural dura, promote host cell adhesion to the graft, and enhance host cell migration along the graft, an ex vivo model of the surgical repair of a small dural defect was developed.

In a typical procedure, an "artificial dural defect" was introduced into a piece of dura (1 cm×1 cm) by microsurgically cutting a small circular hole, 7 mm in diameter, in the center of the specimen. A nanofiber-based scaffold was then utilized to repair the artificial defect by overlaying the graft onto the dural specimen.

Figure 13:
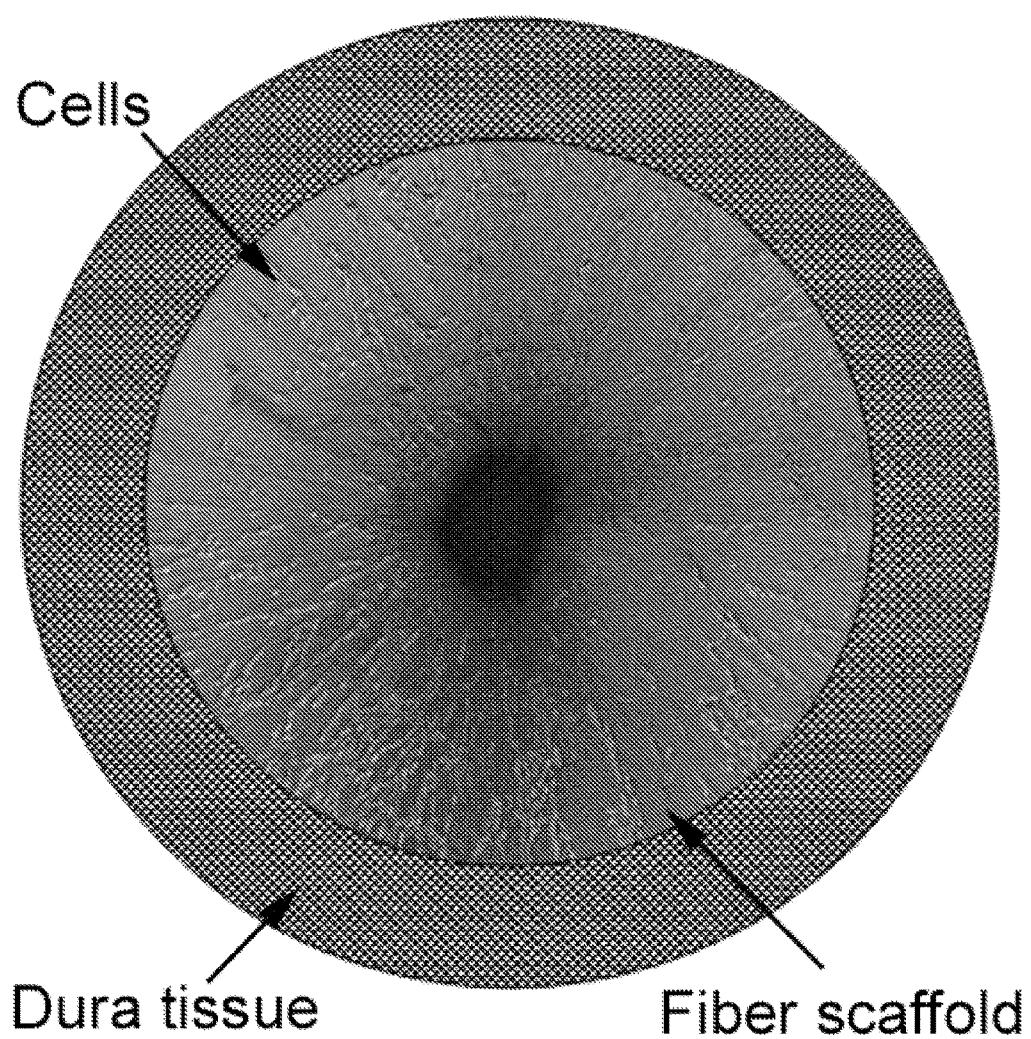
FIG. 13 is a schematic illustration of a cellular infiltration of a biomedical patch from intact dural tissue apposing the edge of a biomedical patch.

FIG. 13 is a schematic illustration of biological cells extending from intact dural tissue, apposed to the edge of a scaffold, into the central portion of the scaffold along radially-aligned nanofibers. The graft covered the entire simulated dural defect while simultaneously contacting the dural tissue at the periphery of the specimen, and demonstrates the ability of native cells in intact tissue to easily adhere to and migrate across the nanofiber scaffolds.

Figure 15A:
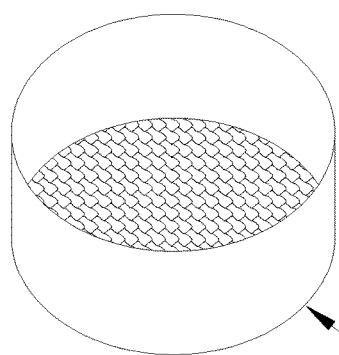
FIG. 15 is a schematic diagram of a custom cell culture system designed to model the wound healing response of defects or voids in a biological tissue.
Figure 15B:
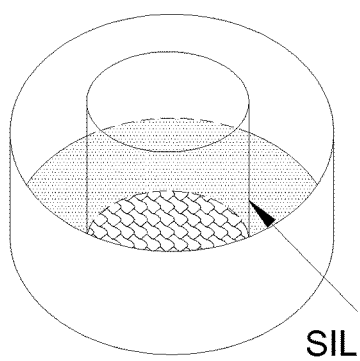
Figure 15C:
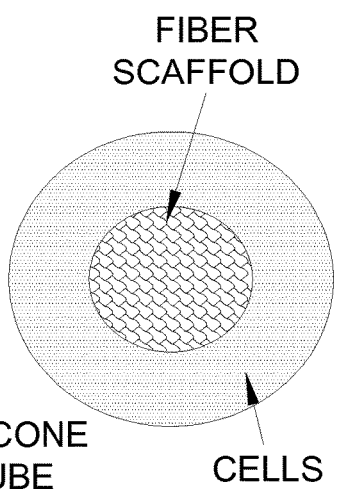

FIGS. 14A-14D are a collection of fluorescence micrographs comparing the migration of cells when dural tissues were cultured on scaffolds of radially aligned nanofibers (FIGS. 14A, 14C) and randomly oriented nanofibers (FIGS. 14B, 14D) for 4 days using a custom cell culture system (FIG. 15). FIGS. 14C and 14D are magnified views of the center portion shown in FIGS. 14A and 14B, respectively. The arrow marks the center of the scaffold.

As shown in FIG. 14A, dural fibroblasts stained with fluorescein diacetate (FDA) migrated from the surrounding tissue along the radially aligned nanofibers and further to the center of the circular scaffold after incubation for 4 days. It was found that the cells could completely cover the entire surface of the scaffold in 4 days. In contrast, a void was observed after the same period of incubation time for a scaffold made of random fibers (FIG. 14B), indicating faster migration of native cells on radially-aligned nanofiber scaffolds than the random counterparts. It is clear that the scaffold made of radially aligned nanofibers (shown in FIGS. 14A and 14C) was completely populated with dural cells which had migrated from the borders of the apposed dural tissue. On the contrary, an acellular region is clearly visible at the center of the scaffold made of randomly oriented nanofibers after the same incubation time, indicating cellular infiltration was incomplete and occurred at a slower rate.

In order to further investigate the effect of fiber alignment and nanofiber scaffold post-modification on cell migration, primary dural fibroblasts isolated from dura tissue were cultured on scaffolds of radially aligned and randomly oriented nanofibers with and without fibronectin coating. FIG. 15 is a schematic diagram of a custom-made cell culture system designed to model wound healing of tissue defects. Specifically, dural fibroblasts were selectively seeded around the periphery of a circular scaffold of nanofibers, effectively forming a 7-mm "simulated dural defect" in the center of the sample.

FIGS. 16A-16D are fluorescence micrographs showing cell morphology and distribution on scaffolds of radially aligned nanofibers (FIGS. 16A, 16C) and randomly oriented nanofibers (FIGS. 16B, 16D) without and with fibronectin coating after incubation for 1 day. As shown in FIG. 16A, many cells could attach to the uncoated scaffolds including radially aligned nanofibers. In comparison, fewer cells poorly attached to the uncoated scaffold of randomly oriented nanofibers and cell aggregations were noticed (FIG. 16B). Seeded cells were distributed evenly over the entire surface of the fibronectin-coated scaffold of radially aligned nanofibers, and they exhibited an elongated shape parallel to the axis of nanofiber alignment (FIG. 16C). This result indicates that fibronectin coating could enhance the influence of topographic cues on cell morphology provided by aligned fibers. The cells could also adhere well to the fibronectin-coated scaffold of randomly oriented nanofibers and cell distribution was more uniform than the uncoated samples, though no cell elongation or alignment was observed (FIG. 16D). The random organization of cells on the randomly-oriented nanofiber scaffolds also mimics the organization of cells in scar tissue. This suggests that the aligned scaffolds may assist in reducing scar tissue formation by promoting more regular cell organization/function.

To characterize cell motility on the scaffold, cells were stained with FDA and fluorescence images were taken at different time points. FIGS. 17A-17D are fluorescence micrographs showing the migration of dura fibroblasts seeded on fibronectin-coated scaffolds of radially aligned nanofibers for 1 day (FIG. 17A), 3 days (FIG. 17B), and 7 days (FIG. 17C). FIG. 17D is a magnified view of FIG. 17C. The cells were radially aligned, replicating the alignment of fibers underneath, as shown in FIG. 17D.

Figure 19:
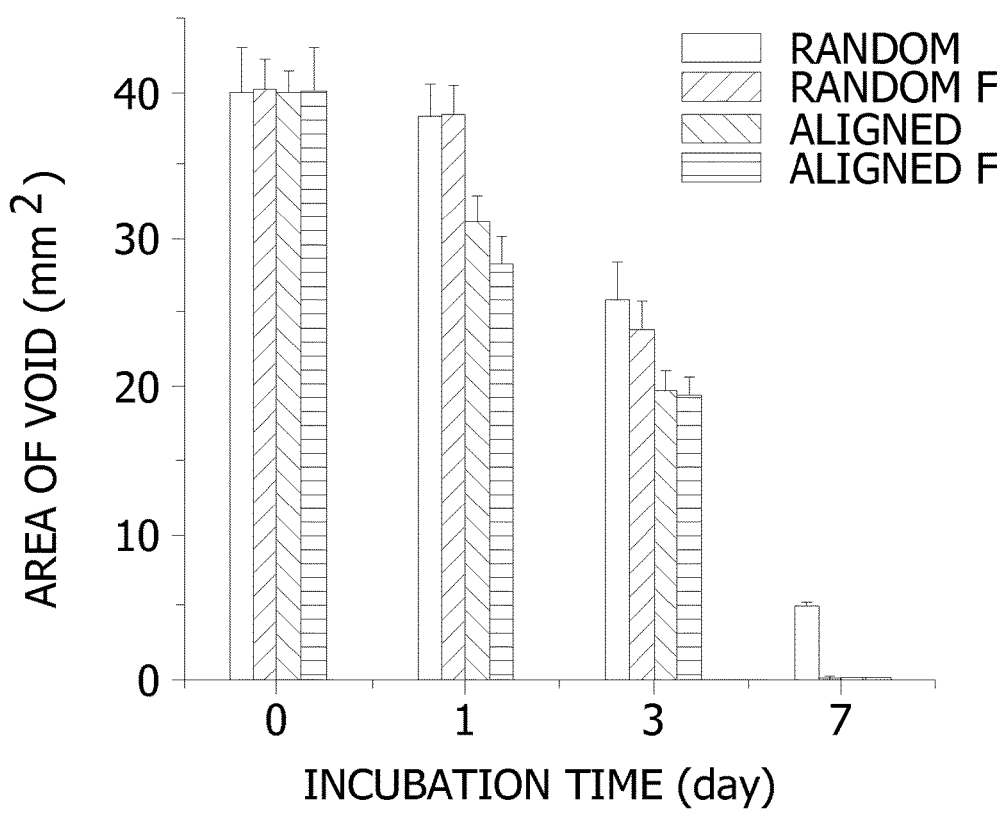
FIG. 19 is a graph illustrating the acellular area remaining on the nanofiber scaffold within the simulated tissue defect as a function of incubation time.

The ability of dural fibroblasts to migrate into and repopulate a simulated dural defect was measured at various time points throughout the experiment as an estimate of the regenerative capacity of the substitute. FIG. 18 is an illustration of the determination (e.g., calculation) of the area of simulated dural defect remaining on the scaffold at a given time point. FIG. 19 is an illustration of the area of void space as a function of incubation time. In FIG. 19, "Random" indicates samples with a scaffold of random fibers; "Random F" indicates samples with a fibronectin-coated scaffold of random fibers; "Aligned" indicates samples with a scaffold of radially aligned fiber; and "Aligned F" indicates samples with a fibronectin-coated scaffold of radially aligned fibers. An asterisk (*) and a hash (#) indicate $p<0.05$ for samples compared with Random samples and Random F samples in the same period of incubation time.

The area of void decreased with increasing incubation time for all the scaffolds tested due to the inward migration of cells. As illustrated by FIGS. 17A-17D, aligned fibers may significantly enhance cell migration compared to random fibers, and cells migrated fastest on the fibronectin-coated scaffold of radially aligned nanofibers for the first 3 days of incubation. Around 5 $mm^2$ of surface area remained uncovered by cells on the uncoated random scaffolds even after incubation for 7 days. In contrast, cells covered almost the entire area of the simulated defect within the same period of incubation for other three types of scaffolds.

FIGS. 20A-20D are fluorescence micrographs showing live dural fibroblasts labeled with membrane dye on scaffolds of radially aligned nanofibers with fibronectin coating after a 1-day culture (FIG. 20A), a 3-day culture (FIG. 20B), a 7-day culture (FIG. 20C), and a 10-day culture (FIG. 20D). FIG. 20 D includes an inset of a high magnification image of FIG. 20D indicating that the cells were radially aligned on the aligned scaffolds. Cell migration towards the center of a fibronectin-coated scaffold of radially aligned nanofibers was further confirmed by time lapse imaging shown in FIGS. 20A-20D.

Dural tissue is primarily composed of type I collagen. The production of type I collagen from dural fibroblasts was also examined. FIGS. 21A-21D are fluorescence micrographs obtained by immunostaining of type I collagen with cell nuclei with 4',6-diamidino-2-phenylindole (DAPI) in blue for scaffolds of radially aligned fibers (FIGS. 21A, 21C) and randomly oriented fibers (FIGS. 21B, 21D). It was observed that comparable levels of type I collagen were produced by cells on the scaffolds of radially aligned fibers as compared to the scaffolds of random fibers although one previous study showed more elongated cells expressed higher collagen type I than did less elongated cells. Additionally, fibronectin coating had no significant influence on the production of type I collagen. The type I collagen was oriented haphazardly for the random scaffolds, resembling the extracellular composition of amorphous scar tissue, and had a high degree of organization for the radially aligned scaffolds, resembling healthy connective tissue Recent advances in cell-biomaterial interaction have shown that both chemical and topographical properties of the materials surface can regulate and control cell shape and function. Cell orientation, motility, adhesion and shape can be modulated by specific surface micro- and nano-topographies. Cells can align along microgrooves or similar topographical features on a surface. It was demonstrated that fibroblasts were the most sensitive cell-type compared to endothelial cells and smooth muscle cells, and responded with a strong alignment, elongation, and migration along such topographical features.

Simultaneously, electrospinning has been widely used for producing nanofibers for a rich variety of applications in tissue engineering including skin grafts, artificial blood vessels, nerve repair, and others. Yet previous studies were limited to the use of scaffolds made of random and uniaxially-aligned nanofibers. Scaffolds composed of uniaxially-aligned nanofibers are not practical for wound healing applications due to the commonality of irregularly shaped wounds. The work described herein demonstrated for the first time the fabrication of a new type of scaffolds made of radially aligned nanofibers. This novel type of scaffold can guide dural fibroblasts spreading along the direction of fiber alignment and direct cell motility towards the center of the scaffold, resulting in faster cell migration and infiltration compared to scaffolds composed of randomly oriented nanofibers.

In addition, uniaxially aligned nanofiber scaffolds cannot match such a capability in that they can guide cell migration only in one direction. It was reported that controlling cellular orientation or morphology by topography, the so-called "contact guidance", could allow for the organization of extracellular matrix. For most injuries, repair results in previously functional tissue becoming a disorganized amalgam of cell (e.g., fibroblasts) and extracellular matrix (e.g., collagen fibers) known as a scar. Highly organized cells and extracellular matrix is required for proper tissue regeneration and function, which is normally vastly different from tissue repair with scarring. It has been demonstrated in the present work that extracellular matrix type I collagen on scaffolds of radially aligned nanofibers showed a high degree of organization, suggesting that radially-aligned nanofiber scaffolds may reduce the possibility of scar tissue formation following wound healing.

A dura substitute should be safe, efficacious, easy to handle, watertight, and easily integrated into the surrounding tissue to form new tissue similar to the native tissue. Also, it should avoid harmful foreign body reactions, be free of any potential risk of infections, have mechanical properties similar to those of natural dura mater, in particular with respect to flexibility and strength, be stable and/or storable, and be available for immediate use. In the present work, biodegradable polymer PCL was chosen as a material for dural substitute in that PCL has some advantages compared with other bioabsorbable polyesters. Heterogeneous degradation of PGA and poly(L-lactic acid) (PLLA) could lead to a sudden increase of degradation products, resulting in acidic conditions and toxic reactions in the surrounding tissue. The degradation of PCL is slower and produces less-acidic degradation products and has been studied as a wound dressing materials since the 1970s.

In order to obtain water-tight property, the radially-aligned nanofiber scaffold can be combined with nonwoven mat to form two-layered or even multi-layered substitutes. Simultaneously, antibiotics can be readily encapsulated inside nanofibers to further reduce inflammatory response, improve wound healing, and prevent postsurgery adhesion. Alternatively, PCL can be blended with other polymers to further improve its biocompatibility, as well as mechanical, physical, and chemical properties. Moreover, extracellular proteins and/or growth factors can be immobilized on the surface of the nanofibers using various surface modification approaches to enhance cell adhesion. The current work demonstrates the effect of fibronectin coating on the PCL nanofibers through electrostatic interaction on dural fibroblast adhesion and motility. The results presented herein demonstrate that fibronectin coating enhanced adhesion of dural fibroblasts and improved cell migration on randomly oriented nanofiber scaffolds. In contrast, the coating had marginal contribution to cell motility on radially aligned nanofiber scaffolds, compared to the bare scaffolds, indicating the predominant role played by nanofiber alignment and resulting surface topography.

In summary, the fabrication of a new type of electrospun nanofiber scaffold including radially aligned fibers and the potential application of such structures as dural substitutes are described herein. Dural fibroblasts cultured on scaffolds of radially aligned nanofibers were elongated parallel to the fiber axis, and cell migration towards the center of the scaffold was accelerated along with the development of a regular arrangement of extracellular matrix like type I collagen, potentially promoting fast regeneration and formation of neodura. Taken together, these results suggest that radially aligned nanofibers possess great potential as an artificial dural substitute, may offer an alternative in the repair of dural defects, and furthermore occupy a unique, desirable niche within the neurosurgical community.

Additional Experimental Results

In a typical procedure for electrospinning PCL (Mw=65 kDa, Sigma-Aldrich) nanofibers, a solution of 20% (w/v) PCL in a mixture of dichloromethane (DCM) and N,N-dimethylformamide (DMF) (Fisher Chemical) with a volume ratio of 8:2 was used. The fibers were spun at 10-17 kV with a feeding rate ranging from 0.5 mL/h, together with a 23 gauge needle as the spinneret. A piece of aluminum foil was used as a collector to obtain random nanofiber scaffolds. Radially aligned nanofiber scaffolds were fabricated utilizing a collector consisting of a ring electrode (e.g., metal ring) and a point electrode (e.g., a sharp needle). Electrospun PCL nanofibers were coated with fibronectin (Millipore, Temecular, Calif.) as the following. The electrospun fiber scaffolds were sterilized by soaking in 70% ethanol overnight and washed three times with phosphate buffered saline (PBS). Then, the scaffolds were immersed in a 0.1% poly-$_L$-lysine (PLL) (Sigma-Aldrich) solution for one hour at room temperature, followed by washing with PBS buffer (Invitrogen) three times. Subsequently, the samples were immersed in a fibronectin solution (26 μL 50 μg/mL fibronectin solution diluted with 5 mL PBS buffer) at 4° C. overnight. Prior to cell seeding, the fibronectin solution was removed and the nanofiber scaffolds were rinsed with PBS buffer.

The PCL nanofiber scaffolds were sputter-coated with gold before imaging with scanning electron microscope (Nova 200 NanoLab, FEI, Oregon, USA) at an accelerating voltage of 15 kV. Samples prepared for use in cell culture were inserted into a 24-well TCPS culture plate and sterilized by soaking scaffolds in 70% ethanol.

Fibroblasts were isolated from sections of explanted dura. Specifically, a 2.0 cm×1.5 cm section of dura was removed through sharp dissection and washed three times with cold PBS. Dural fibroblasts were then isolated by digesting minced dura three times in 4 mL of warm Hank's Balanced Salt Solution (HBSS) containing 0.05% Trpsin and 0.04% EDTA (Sigma-Aldrich, St. Louis, Mo.). Following digestion collected supernatant was centrifuged and the pellet of dural cells was isolated and resuspended in Dulbecco's modified Eagle's medium (DMEM) supplemented with 10% calf serum and 1% penicillin and streptomycin. Dural cells obtained in this manner were then plated in 75 cm$^2$ flaks and expanded (subpassaged no more than 5 times).

Large, continuous pieces of dura mater were placed in cold PBS and microsurgically trimmed into 1 cm×1 cm sections. An artificial defect was then introduced into each section of dura by microsurgically cutting a small circular hole, 7 mm in diameter, in the middle of the section. Sections of dura were then introduced into individual wells of 6-well culture plates containing 4 mL of DEMEM supplemented with 10% calf serum and 1% penicillin and streptomycin. Random and radially aligned nanofiber scaffolds 1 cm in diameter were then utilized to repair the artificial defects by overlaying the graft onto the dural specimen. Nanofiber scaffolds were placed on the dura such that the graft covered with entire defect while simultaneously contacting the dural tissue at the periphery of the specimen. Nanofiber scaffolds were held in this position throughout the experiment by placing a sterilized metal ring over both the scaffold and the dura. After 4 days of culture, the cells were stained with FDA in green color and imaged with fluorescence microscope. Fluorescent images were taken using a QICAM Fast Cooled Mono 12-bit camera (Q Imaging, Burnaby, BC, Canada) attached to an Olympus microscope with OCapture 2.90.1 (Olympus, Tokyo, Japan). Similarly, around 1×10$^5$ dural fibroblast cells were seeded onto the periphery of nanofiber scaffolds using the custom-made culture system shown in FIG. 15. After different periods of time, the cells were stained with FDA in green color and imaged with fluorescence microscope. The total surface area of nanofiber scaffold devoid of migrating cells was then quantified using Image J software (National Institute of Health).

Living cells were labeled with membrane dye using VYBRANT DiO cell-labeling solution (Invitrogen) according to the manufacturer's instructions and then imaged at day 1, 3, 7, and 10.

Production of collagen type I by the dural fibroblasts on the fiber scaffolds was assessed using immunohistochemistry. At day 7, the cells were rinsed with PBS and fixed with 3.7% formalin for 1 h (N=4). Cells were permeabilized using 0.1% Triton X-100 (Invitrogen) in PBS for 20 min, followed by blocking in PBS containing 5% normal goat serum (NGS) for 30 min. Monoclonal antibodies for type I collagen (1:20 dilution) was obtained from EMD Chemicals (Calbiochem, San Diego, Calif.). Cells were washed three times with PBS containing 2% FBS. The secondary antibody GtxRb IgG Fluor (Chemicon, Temecula, Calif.) (1:200 dilution) was applied for 1 h at room temperature. Fluorescent images were taken using a QICAM Fast Cooled Mono 12-bit camera (Q Imaging, Burnaby, BC, Canada) attached to an Olympus microscope with OCapture 2.90.1 (Olympus, Tokyo, Japan).

Mean values and standard deviation were reported. Comparative analyses were performed using the Turkey post hoc test by analysis of variance at a 95% confidence level.

As a secondary study, an ex vivo model of the surgical repair of a small dural defect was developed. Large pieces of healthy dura mater (3 cm×3 cm) were placed into cold, supplemented Dulbecco's Modified Eagle Media (DMEM) and microsurgically trimmed into smaller (1 cm×1 cm) pieces. Artificial defects were introduced into the pieces of dura by microsurgically cutting small circular holes, 6-8 mm in diameter, into the middle of the specimens. Radially aligned nanofiber scaffolds, randomly oriented nanofiber scaffolds, and DURA MATRIX collagen scaffolds (1 cm×1 cm) were then utilized to repair the artificial defects by overlaying the graft onto the dural specimen, such that the graft covered the entire defect while simultaneously contacting the dural tissue at the periphery of the specimen.

Assemblies of dural/dural substitute were then cultured in vitro in supplemented DMEM for a period of four days. At the terminal time point, optical and fluorescent microscopy was utilized to assess the regenerative capacity of the substitute, defined as the ability of dural cells to migrate onto the artificial substrate and repopulate the acellular region of the dural substitute within the artificial defect.

Results demonstrated that native cells present in intact dura (primarily dural fibroblasts) readily migrated onto apposed polymeric nanofiber dural substitutes in high concentrations within 24 to 48 hours after coming into contact with pieces of explanted dura. Dural cell migration onto gold-standard collagen matrices followed a similar time course, though slightly lower concentrations of dural cells were observed migrating onto collagen matrices compared to nanofiber dural substitutes. This observation suggests that nanofiber dural substitutes easily adhere to native dural tissue, an important quality regarding the intraoperative handling and/or placement of the material, and that nanofiber dural substitutes provide an ideal substrate for dural fibroblast adhesion.

Further examination of the various dural substitutes after four days of culture revealed that dural fibroblast migration into the central, acellular region of the material proceeded significantly faster on radially aligned nanofiber substitutes than on randomly oriented nanofiber substitutes or collagen matrices. This finding was evidenced by the fact that after four days of culture, a prominent acellular region ("void space") remained on samples of both the random nanofiber substitute and the collagen matrix.

In contrast, samples of radially aligned nanofiber materials examined at the same time point were completely populated with dural cells which had migrated from the borders of the apposed dural tissue. In effect, radially aligned nanofiber substitutes were able to induce significantly faster "healing" of this simulated dural defect than both randomly oriented materials. High magnification views of dural substitutes within this ex vivo culture further demonstrated the ability of radially aligned nanofiber materials to align and direct native, migratory dural cells, a result similar to that of the previous study conducted using pre-seeded dural fibroblasts. Specifically, dural cells were noted to align and extend parallel to individual nanofibers within the artificial substrate, as well as deposit organized extracellular matrix proteins (namely type I collagen) on the aligned nanofiber materials. This observation suggests that the topographical cues presented by aligned nanofiber substitutes are capable of organizing and directing native dural cells migrating from intact dura, and may enhance the ability of these migratory cells to deposit extracellular matrix proteins necessary to heal and repair dural defects.

Results of this secondary study demonstrate that nanofiber dural substitutes not only provide a favorable scaffold for dural cell adhesion and migration, but readily support the ingrowth of dural cells from whole, intact dura mater. The ability of nanofiber materials to intimately interface intact dura mater and facilitate rapid cellular population of the polymeric scaffold strongly suggest that this material may function exceptionally well as an artificial graft in the surgical repair of complex dural defects. In addition, dural substitutes constructed of radially aligned nanofibers were demonstrated to promote faster "healing" of simulated dural defects than randomly oriented materials, suggesting that aligned nanofiber scaffolds imparting nanoscale topographical features may represent a significant technological advance over clinical gold-standard collagen matrices.

Although experiments described herein were limited in duration, the results of these experiments suggest that biomedical patches including radially aligned fibers are viable for use in tissue repair at longer durations. For example, it is expected that the observed accelerated cellular ingrowth would continue until the biological tissue at the site of a defect is completely regenerated and/or until degradation of the biomedical patch is complete.

In Vivo Experimental Results

In vivo experimentation was performed by imposing a 12 millimeter diameter dural defect in native porcine dura. The defect was repaired with a collagen dural substitute, a mono-layer dural substitute with randomly oriented nanofibers, and a bi-layer dural substitute with one layer of radially aligned nanofibers fused to a second layer of randomly oriented nanofibers through layer-by-layer stacking (e.g., as described above with reference to FIG. 8). In a control group, the defect was unrepaired.

Figure 22:
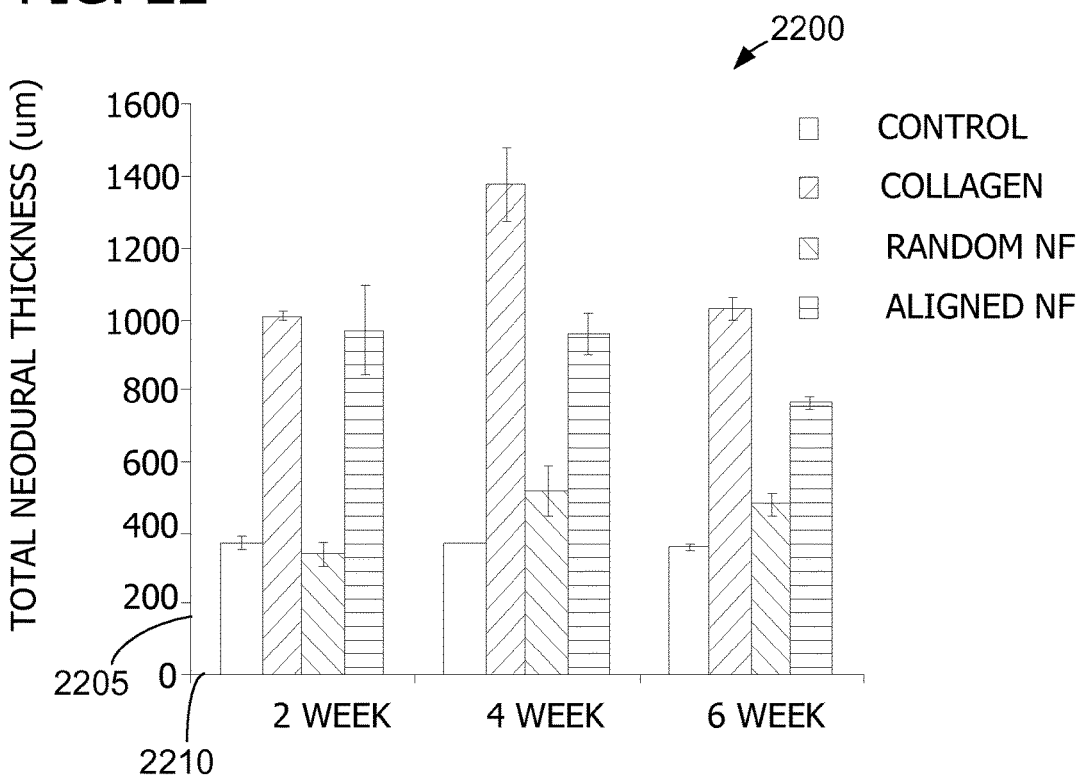
FIG. 22 is a graph illustrating the thickness of regenerated dura at the center of repaired dural defects over time.

FIG. 22 is a graph 2200 illustrating the thickness of regenerated dura at the center of repaired dural defects over time. In graph 2200, a y-axis 2205 represents the total thickness of regenerated dura, including both regenerative tissue and the integrated dural substitute material, at the center of a dural defect. Samples with no dural substitute (control samples), a collagen dural substitute, a mono-layer randomly oriented nanofiber dural substitute, and a bi-layer radially aligned nanofiber dural substitute are grouped by elapsed time on an x-axis 2210.

Figure 23:
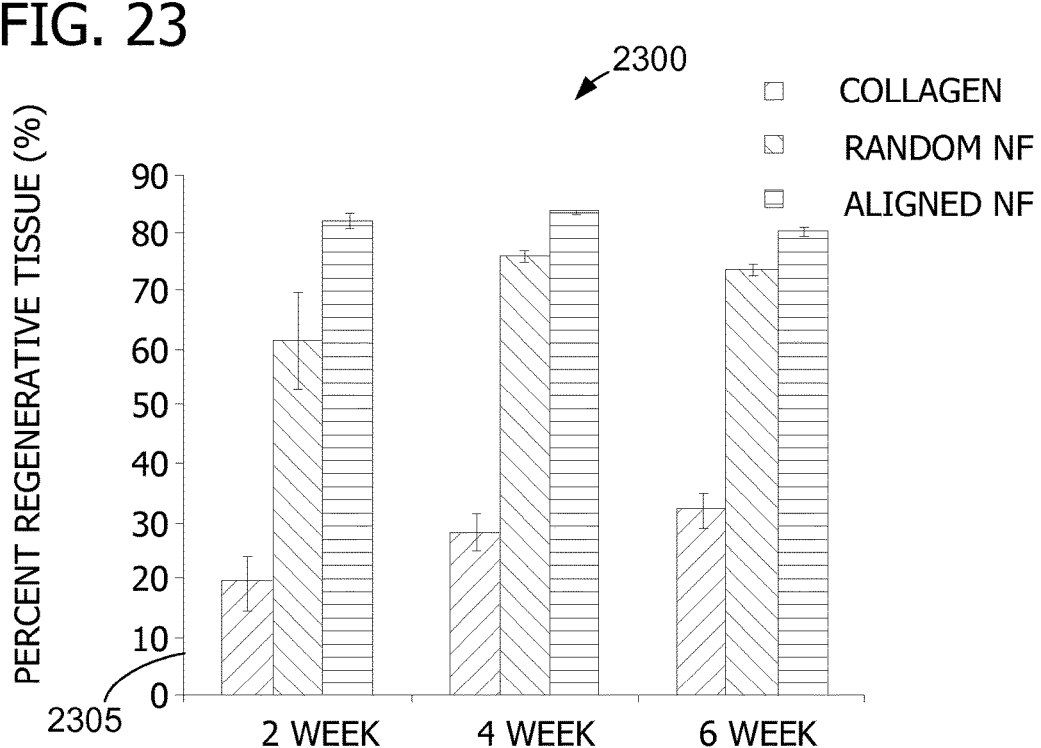
FIG. 23 is a graph illustrating regenerative collagenous tissue content over time.

FIG. 23 is a graph 2300 illustrating regenerative collagenous tissue content over time. In graph 2300, a y-axis 2305 represents the percentage of regenerated dura that is composed of regenerative collagenous tissue. Samples with a collagen dural substitute, a mono-layer randomly oriented nanofiber dural substitute, and a bi-layer radially aligned nanofiber dural substitute are grouped by elapsed time on an x-axis 2310.

Electrode Arrays

In some embodiments, a collector includes a plurality of electrodes at least partially circumscribing an area and a second electrode positioned within the area. The electrodes may be arranged in an array, such as a grid and/or other polygonal pattern, and a polymer deposited on the electrodes may form fibers extending between the electrodes of the collector, such that the fibers define the sides of a plurality of polygons, with the electrodes positioned at the vertices of the polygons. In some embodiments, the structure created by such fibers may be used to create a cell microarray, such as by seeding the structure with cells and incubating the cells to promote propagation of the cells throughout the structure.

Cell microarrays may provide powerful experimental tools for high-throughput screening useful in a number of applications ranging from drug discovery and toxicology to stem cell research and tissue engineering. For example, cell microarrays may represent an effective means of fabricating ordered neuronal networks useful in studying synapse formation and neuronal plasticity in vitro. At least some known techniques for fabrication of neuronal microarrays have concentrated on the use of spatial patterning of cell adhesive and/or cell repulsive materials and agents. Unfortunately, such fabrication techniques may be time consuming and costly, and involve the use of sophisticated instrumentation (e.g., photolithography, soft lithography, contact printing, microfluidics, nanoprinting, and inkjet printing).

Electrospinning is capable of producing one-dimensional fibers with diameters ranging from several nanometers to several microns. The large surface area to volume ratio and nanoscale morphology of electrospun nanofibers may suggest that these materials effectively mimic the architecture of extracellular matrix (ECM). As a result, electrospun nanofiber materials have been utilized in a wide variety of biomedical applications. Electrospun nanofibers may be deposited on a conductive collector in a random fashion and/or aligned into uniaxial arrays through manipulation of an electric field and/or application of mechanical force.

Embodiments described herein facilitate producing a complex cell microarray using electrospun nanofibers. In exemplary embodiments, a collector with an array of electrodes is used to fabricate electrospun nanofiber scaffolds that include a complex, ordered architecture and numerous multiwells. Such a scaffold may be valuable at least for i) cell microarray formation; and ii) neuronal network formation. The use of presented complex nanofiber arrays may facilitate the creation of advanced substrates useful in neural engineering applications and cell arrays useful in bio-sensing and drug screening applications.

Figure 24:
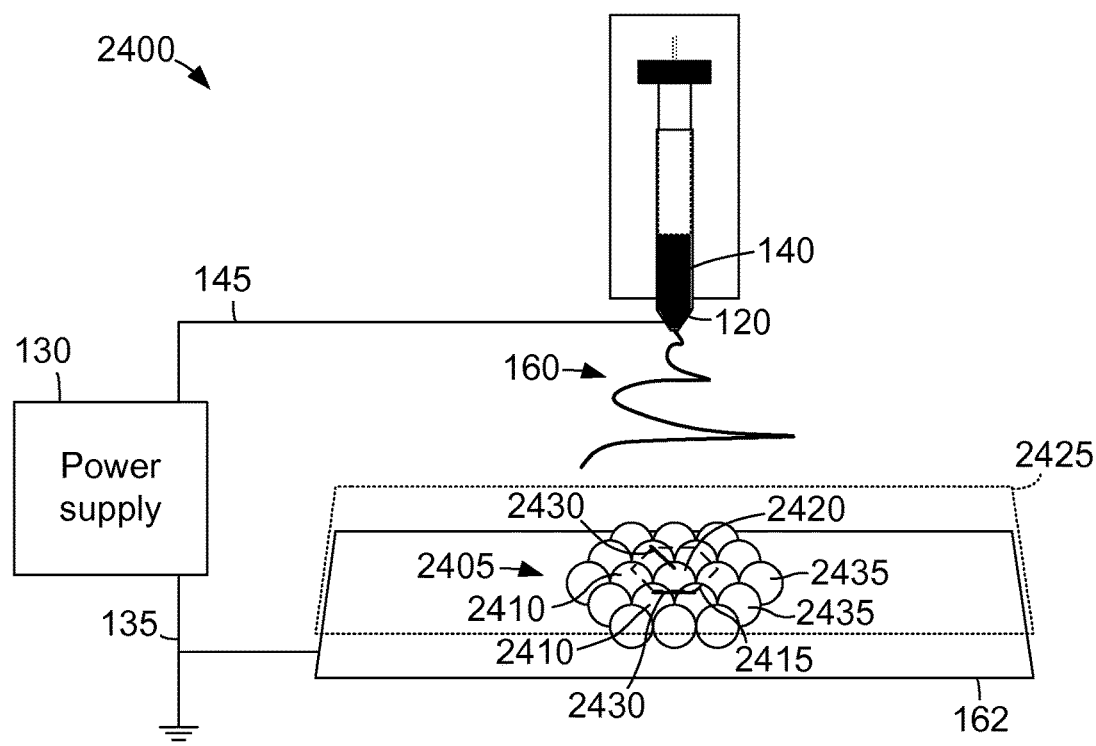
FIG. 24 is a diagram illustrating a perspective view of an example electrospinning system for producing a structure of fibers aligned in polygons using an array of electrodes.

FIG. 24 is a diagram illustrating a perspective view of an example electrospinning system 2400 for producing a structure of polygonally aligned fibers using an array of electrodes. System 2400 is similar to system 100 (shown in FIG. 1) in structure and operation. A collector 2405 includes a plurality of first electrodes 2410, which may be referred to as peripheral electrodes. First electrodes 2410 define and/or at least partially circumscribe an area 2415, such as a polygon. As illustrated in FIG. 24, the area 2415 defined by first electrodes 2410 is a hexagon. A second electrode 2420, which may be referred to as an inner electrode, is positioned within (e.g., approximately at the center of) area 2415, such that first electrodes 2410 surround second electrode 2420. In exemplary embodiments, first electrodes 2410 and second electrodes are metallic (e.g., stainless steel) beads having a diameter between 0.5 millimeters (mm) and 5.0 mm (e.g., 1.0 mm or 2.0 mm).

System 2400 also includes a spinneret 120 and is configured to create an electric potential between collector 2405 and spinneret 120, as described above with reference to FIG. 1. In exemplary embodiments, peripheral electrodes 2410 and inner electrode 2420 are electrically coupled to a power supply 130 via a conductor 135, and spinneret 120 is coupled to power supply 130 via a conductor 145. Power supply 130 is configured to charge peripheral electrodes 2410 at a first amplitude and/or polarity via conductor 135, and to charge spinneret 120 at a second amplitude and/or polarity, opposite the first polarity, via conductor 145.

In the embodiment illustrated in FIG. 24, peripheral electrodes 2410 and inner electrode 2420 are metallic (e.g., stainless steel) beads or balls, which may be referred to as "microbeads," arranged in a hexagonal pattern. In some embodiments, circular enclosed area 125 may have a diameter of between 1 centimeter and 20 centimeters. In other embodiments, peripheral electrodes 2410 and inner electrode 2420 may be any shape and/or may be arranged in any pattern suitable for use with the methods described herein. For example, peripheral electrodes 2410 and inner electrode 2420 may be pins, rods, domes, and/or ridges. Further, peripheral electrodes 2410 and inner electrode 2420 may be arranged in an octagonal, pentagonal, and/or square pattern, for example, though other polygonal and non-polygonal arrangements, regular and/or irregular, are also contemplated.

In one embodiment, area 2415 defines a horizontal plane 2425. Spinneret 120 is aligned with inner electrode 2420 and vertically offset from horizontal plane 2425 at a variable distance. For example, spinneret 120 may be vertically offset from horizontal plane 2425 at a distance of 1 centimeter to 100 centimeters. In exemplary embodiments, inner electrode 2420 and/or peripheral electrodes 2410 include a rounded (e.g., convex) surface, such as the surface of the metallic beads shown in FIG. 24, oriented toward horizontal plane 2425.

As described above with reference to FIG. 1, spinneret 120 is configured to dispense a polymer 140 while spinneret 120 is electrically charged at the second amplitude and/or polarity, and peripheral electrodes 2410 and inner electrode 2420 are electrically charged at the first amplitude and/or polarity. Spinneret 120 dispenses polymer 140 as a stream 160. Stream 160 has a diameter approximately equal to the aperture diameter of spinneret 120. Stream 160 descends toward collector 2405. For example, stream 160 may fall downward under the influence of gravity and/or may be attracted downward by a charged conductive surface 162 positioned below collector 2405. For example, conductive surface 162 may be electrically coupled to conductor 135 and charged at the same amplitude and/or polarity as peripheral electrodes 2410 and central electrode 2420. As stream 160 descends and is deposited on collector 2405, polymer 140 forms one or more solid polymeric fibers 2430 extending from inner electrode 2420 to a peripheral electrode 2410 and/or between peripheral electrodes 2410.

In some embodiments, collector 2405 includes peripheral electrodes 2410 that define a plurality of areas 2415. For example, peripheral electrodes 2410 immediately surrounding inner electrode 2420 may be considered inner peripheral electrodes, and a plurality of outer peripheral electrodes 2435 may surround inner peripheral electrodes 2410, such that inner peripheral electrodes 2410 are nested within outer peripheral electrodes 2435. Collector 2405 may include any quantity of nested sets of peripheral electrodes. While collector 2405 includes electrodes in a closely-packed arrangement (e.g., with electrodes contacting each other), it is contemplated that electrodes may be displaced from each other by an inter-electrode distance, which may be constant throughout the collector or may vary between different pairs of electrodes.

Figure 25:
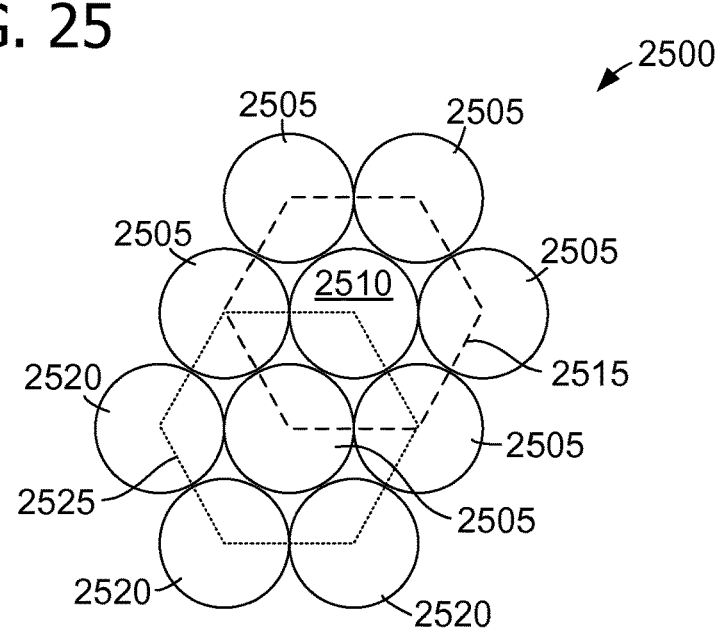
FIG. 25 is a diagram illustrating an elevation view of an example modular electrospinning collector.

Further, in some embodiments, a collector may include electrodes that define a plurality of partially overlapping areas in a modular fashion. FIG. 25 is a diagram illustrating a perspective view of an example modular electrospinning collector 2500. Collector 2500 includes first electrodes 2505 surrounding a second electrode 2510. First electrodes 2505 define a first hexagonal area 2515. With respect to first hexagonal area 2515, second electrode 2510 may be considered an inner electrode, and first electrodes 2505 may be considered peripheral electrodes.

Collector 2500 also includes a plurality of third electrodes 2520 that are positioned outside first hexagonal area 2515. Third electrodes 2520, second electrode 2510, and a subset of first electrodes 2505 define a second hexagonal area 2525 that partially overlaps first hexagonal area 2515. One of the first electrodes 2505 (e.g., a peripheral electrode with respect to first hexagonal area 2515) is positioned within second hexagonal area 2525. With respect to second hexagonal area 2525, this first electrode 2505 may be considered an inner electrode. Third electrodes 2520, the subset of the first electrodes 2505, and the second electrode 2510 may be considered peripheral electrodes. Although electrodes defining two partially overlapping areas are illustrated in FIG. 25, it is contemplated that the modular nature of collector 2500 facilitates including any quantity of electrodes that define any quantity of areas, such that collector 2500 may be extended in one or more directions by adding electrodes to the perimeter of collector 2500.

As described above with reference to system 2400 (shown in FIG. 24), collector 2500 (e.g., first electrodes 2505, second electrode 2510, and third electrodes 2520) is configured to be electrically charged at an amplitude and/or a polarity opposed the amplitude and/or polarity at which spinneret 120 is electrically charged. When these components are so charged, a polymer dispensed by spinneret 120 may form fibers extending between the electrodes (e.g., first electrodes 2505, second electrode 2510, and/or third electrodes 2520) of collector 2500.

Figure 26:
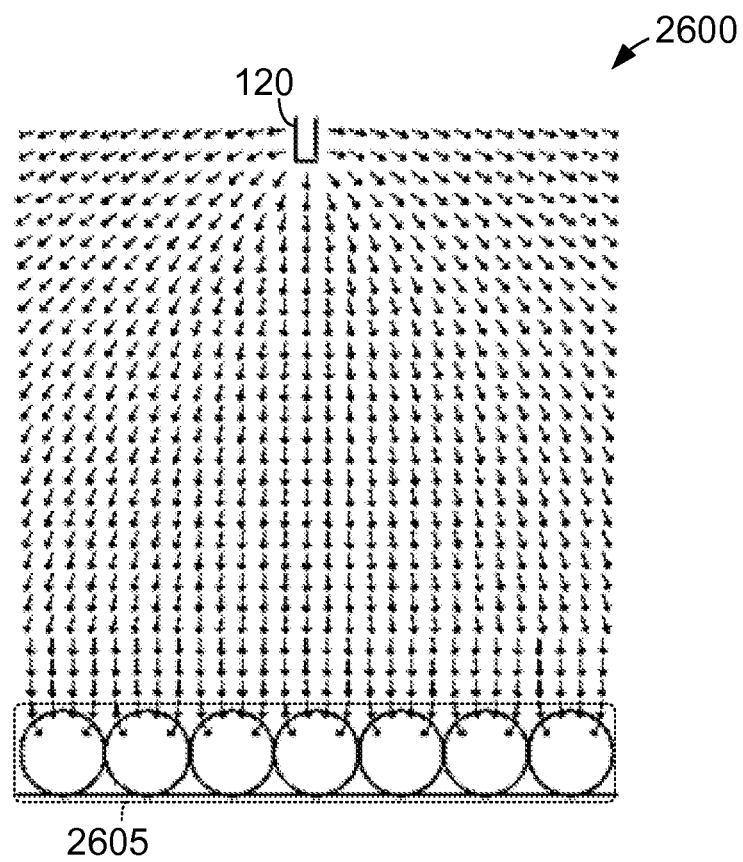
FIG. 26 is a diagram illustrating an electric field generated by an electrospinning system such as the electrospinning system shown in FIG. 24.

FIG. 26 is a diagram 2600 illustrating an electric field generated by an electrospinning system such as electrospinning system 2400 (shown in FIG. 24). Diagram 2600 shows a two dimensional, cross-sectional view of electric field strength vectors between a spinneret 120 and a plurality of electrodes 2605.

Electric field vectors near the surface of electrodes 2605 are oriented perpendicular to the surface of electrodes 2605. Electric field vectors between two neighboring electrodes split into two main streams, pointing towards the centers of the two adjacent electrodes 2605. Accordingly, fibers deposited on the surface of electrodes 2605 may be randomly distributed, while the fibers deposited in the region between two neighboring electrodes 2605 may be uniaxially aligned between these two adjacent electrodes 2605.

FIGS. 27A-27F are microscopy images of a nanofiber membrane 2705 produced using a collector with an array of electrodes, such as collector 2405 (shown in FIG. 24). For example, membrane 2705 may be produced using an array of stainless steel beads. FIG. 27A is an optical microscopy image of a membrane 2705. FIG. 27A includes an inset 2710 illustrating a magnification of membrane 2705 with a light source on the right-hand side of the image. Shadows in inset 2710 indicate wells within membrane 2705, the positions of which correspond to the positions of electrodes in the collector.

FIG. 27B is a scanning electron microscopy (SEM) image of membrane 2705 illustrating the complex, ordered architecture composed of hexagonally arranged wells 2715 connected with uniaxially aligned fiber arrays 2720. The depth of the wells formed by depositing electrospun nanofibers on packed stainless steel microbeads 1.0 mm and 2.0 mm in diameter was approximately 200 micrometers (μm) and 400 μm, respectively. Such wells may be referred to as "microwells."

FIGS. 27C-27F are magnifications of corresponding areas within FIG. 27B. FIG. 27C suggests that the fibers deposited on the surface of microbead electrodes were randomly distributed. FIG. 27D shows that the fibers at the interface between the surface of an electrode and a gap between electrodes transitioned from a random orientation to an aligned orientation. FIG. 27E indicates that fibers deposited along the axis connecting the centers of two adjacent electrodes were uniaxially aligned parallel to that axis. FIG. 27F shows that the fiber density was significantly lower between neighboring beads and away from the axes connecting the centers of adjacent beads than in other regions (e.g., shown in FIGS. 27C-27E), and that fiber deposited in this region were randomly oriented.

In some embodiments, a fiber membrane, such as membrane 2705, may be combined with other membranes. For example, a membrane with a plurality of wells interconnected by uniaxially aligned fibers may be used as one layer within a multi-layer structure, as described above with reference to FIG. 8. In addition, or alternatively, different collector types may be combined, such as by using an electrode array collector as an inner collector (e.g., corresponding to a center of a biomedical patch, and using a ring-type collector (e.g., as shown in FIG. 1) as an outer collector that surrounds the inner collector.

Experimental Results

Fiber membranes, or "scaffolds," produced by an electrode array collector as described above were evaluated for use as substrates for generating cell microarrays. Cells were selectively seeded onto the surface of the scaffold by placing a small amount of media, containing specified number of cells, onto the microwells present within the nanofiber arrays.

FIGS. 28A-28D are microscopy images illustrating cell growth in a membrane such as membrane 2705 (shown in FIGS. 27A-27F). FIG. 28A is an optical microscopy image illustrating that droplets 2805 containing cells may be placed within the wells of a fiber membrane. Further, hydrophobic fibers may facilitate maintaining such droplets for over two hours. Cells adherent to the nanofiber matrices after two hours were found to be loosely attached and were easily removed using PBS buffer, suggesting fast, reversible binding of cells within the microarrays. Cells adherent to the nanofiber matrices after twenty-four hours were stained with fluorescein diacetate (FDA) in green to identify living cells.

FIGS. 28B-28D are fluorescence microscopy images illustrating cell microarrays. Live MG-63 cells were stained with fluorescein diacetate and are shown as light areas against a dark background in FIGS. 28B-28D.

FIG. 28B shows an array of cells selectively adhered to the microwells within the nanofiber membrane. Each well within the scaffold was observed to contain approximately 45 cells, while very few cells were observed outside of the microwells within the fiber membrane. The average number of cells adherent on each microwell was easily manipulated by controlling the density of cells present within the seeding droplets.

FIG. 28C demonstrates cell microarrays seeded with greater numbers of cells (approximately 150 cells per well) than were used in the arrays shown in FIG. 28B. Despite increasing cell concentrations, cells remained greatly confined to the wells in the nanofiber scaffold. FIG. 28D shows the same cell microarray shown in FIG. 28C after incubation for three days. Comparison of FIG. 28D to FIG. 28C demonstrates that seeded cells were capable of proliferating and migrating on the surface of the nanofiber scaffolds, yet generally remained physically confined within the wells of the cell microarray.

In order to examine the potential of these unique nanofiber scaffolds as effective substrates for neural engineering applications, dorsal root ganglia (DRG) were seeded onto fiber membranes functionalized with polylysine and laminin and incubated for 6 days. Resulting neurite fields protruding from DRG were stained with anti-neurofilament 200 to visualize neurite extension along the underlying nanofiber scaffold.

FIGS. 29A and 29B are microscopy images illustrating neurite propagation in a membrane such as membrane 2705 (shown in FIGS. 27A-27F). FIG. 29A is an overlay of an optical microscopy image and a fluorescence microscopy image illustrating that neurites emanated from a DRG main body located at the center of FIG. 29A and formed an appreciable neuronal network after 6 days of culture. Neurites were observed to grow along the long axes of uniaxially aligned nanofibers and reach neighboring microwells, effectively replicating the geometry of the underlying nanofiber architecture.

FIG. 29B is an overlay of an optical microscopy image and a fluorescence microscopy image adjacent to the region shown in FIG. 29A. FIG. 29B demonstrates that neurites may continue growing along the direction of uniaxial alignment of nanofibers after reaching the neighboring wells and navigate to other neighboring wells along the fiber alignment in several directions. Neurites extending to adjacent microwells were subsequently observed to split into five groups following the aligned fiber arrays which connected to a secondary set of adjacent wells, further indicating capability of the scaffold to form a complex neuronal network in vitro.

Figure 30A:
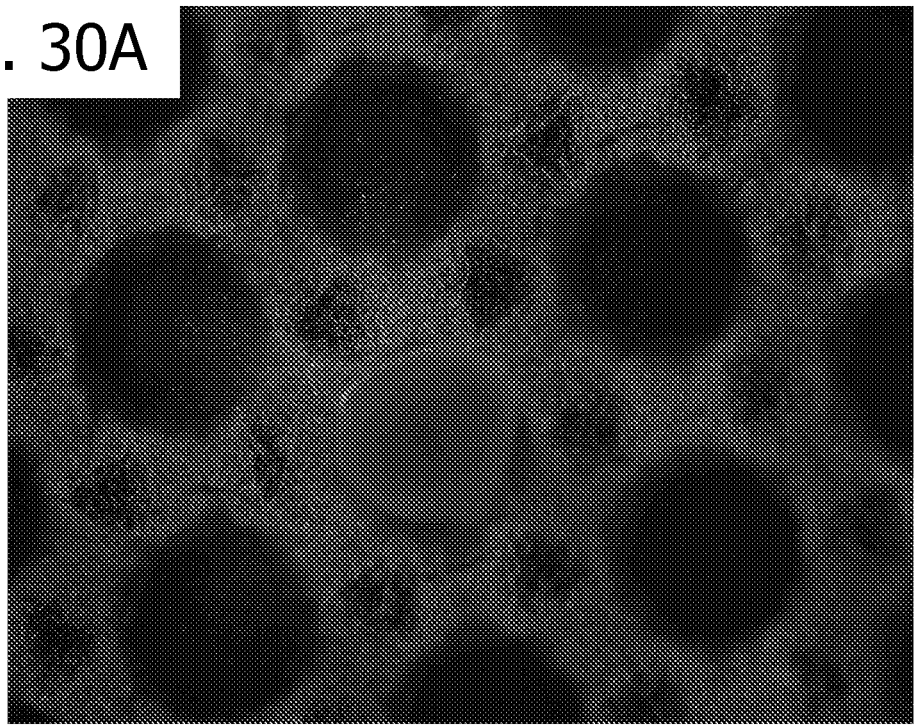
FIGS. 30A and 30B are overlays of an optical microscopy image and a fluorescent microscopy image illustrating neuronal network formation from embryoid bodies in a membrane such as the membrane shown in FIGS. 27A-27F.
Figure 30B:
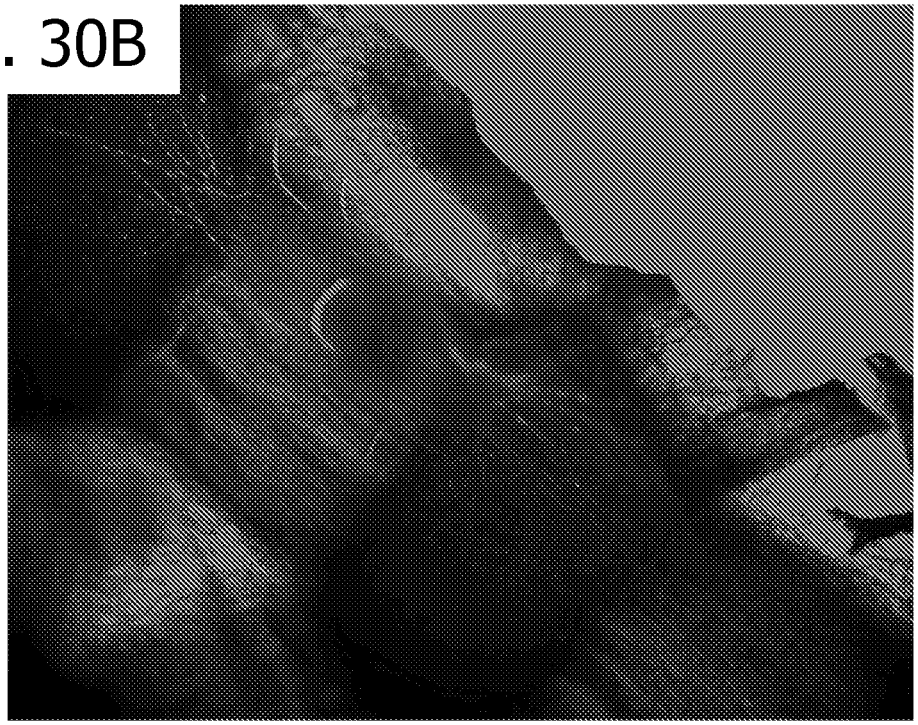

FIGS. 30A and 30B are overlays of an optical microscopy image and a fluorescent microscopy image illustrating neuronal network formation from embryoid bodies in a membrane such as the membrane shown in FIGS. 27A-27F. Embryonic stem (ES) cells, cultured to aggregate into embryoid bodies (EBs) using the 4−/4+ protocol, were seeded onto electrospun nanofiber scaffolds such as that shown in FIGS. 27A-27F, and incubated with B27 supplement to induce neuronal differentiation. Immunostaining with Tuj1, a neuronal marker, was performed after incubation for 14 days to examine the ability of underlying nanofiber scaffolds to promote neuronal differentiation in vitro.

FIGS. 30A and 30B demonstrate the ability of EBs to form neuronal networks on nanofiber membrane substrates. In one case, one EB was confined within one of the microwells, while neurites extended peripherally along the underlying fiber pattern, as shown in FIG. 30A. Neurites extending from cultured EBs were similarly aligned on the uniaxial portion of the scaffold where fibers were highly organized. Upon reaching the region of the adjacent wells, neurites were haphazardly organized as a result of the random orientation of the underlying fibers.

In another case, EBs were seeded on regions of uniaxially aligned nanofibers within the nanofiber array, as shown in FIG. 30B. Neurites again extended along the direction of fiber alignment, and, upon reaching the nearest well, exhibited a disordered organization. Notably, when the neurites extended through the microwell region, their uniaxial alignment, parallel to the underlying fiber alignment, was restored. Together, these results suggest that nanofiber architectures described herein represent a simple and effective means of developing complex neuronal networks from either primary neurons or embryonic stem cells.

Experimental Procedure

The electrospinning system used for fabricating and collecting aligned nanofibers was similar to system 2400 (shown in FIG. 24). The polymer solution used for electrospinning contained 20% PCL (w/v) in a mixed solvent of dichloromethane (DCM) and dimethylformamide (DMF) with a volume ratio of 80:20. The collector included assemblies of stainless steel microbeads with diameters of 1 mm and 2 mm, respectively. The fiber membranes were transferred to culture plates and then fixed by medical grade silicon adhesive. The PCL fibers were sputter-coated with gold before imaging with scanning electron microscope at an accelerating voltage of 15 kV.

For dorsal root ganglia (DRG) culture and immunostaining, DRG were dissected from the thoracic region of embryonic day 8 chicks (E8, stage HH35-36) and collected in Hank's buffered salt solution (HBSS) prior to plating. DRG were seeded on the fiber architectures and incubated for 6 days in modified neurobasal (NB) media containing 1% ABAM, 1% N-2 supplement (Invitrogen), and 30 ng/mL Beta nerve growth factors (B-NGF) (R&D Systems, Minneapolis, Minn.). After incubation for 6 days, the DRG were immunostained with the marker anti-neurofilament 200 (Sigma-Aldrich). Briefly, the DRG were fixed in 3.7% formaldehyde for 45 minutes and permeabilized by 0.1% Triton X-100 for 30 minutes. The samples were blocked in PBS containing 2.5% bovine serum albumin (BSA) (Sigma-Aldrich) for 1 hour. Anti-NF 200 diluted with PBS containing 1.5% BSA was applied to the cells overnight at 4° C. A secondary antibody, AlexaFluor 488 goat anti-mouse IgG (1:200, Invitrogen), was then applied for 1 hour at room temperature. After staining, fluorescence images were captured.

For embryoid body formation and immunostaining, EBs were seeded onto fiber architectures and incubated with neural basal media containing B27 supplement. After 14 days, immunohistochemistry was performed to visualize the spatial distribution of neurites according to our previous study.

The MG-63 cell line was used to demonstrate the formation of cell microarrays. Cells were cultured in alpha minimum essential medium (α-MEM, Invitrogen, Grand Island, N.Y.), supplemented with 10% fetal bovine serum (FBS, Invitrogen) and 1% antibiotics (containing penicillin and streptomycin, Invitrogen). The medium was changed every other day, and the cultures were incubated at 37° C. in a humidified atmosphere containing 5% $CO_2$. A certain number of cells were seeded into each well of the scaffolds by placing small droplets onto wells. After incubation for 2 hours, the scaffolds were washed with culture media to remove the loosely attached cells. Then, the living cells were stained with fluorescein diacetate (FDA) after incubation for 24 hours and imaged with fluorescence microscope.

Additional Electrode Array Arrangements

In addition to particular examples of electrode arrays described above with reference to experimental results, it is contemplated that nanofiber structures such as those described herein may be produced with various other electrode arrays. FIGS. 31A-31D are scanning electron microscopy images illustrating membranes produced using a variety of electrode arrays.

FIG. 31A illustrates a fiber membrane fabricated using a collector composed of hexagonal arrays of stainless steel beads. FIG. 31B illustrates a fiber membrane fabricated using a collector composed of hexagonal arrays of stainless steel beads having a larger diameter than the stainless steel beads used to produce the membrane shown in FIG. 31A.

Other, non-hexagonal, packing orders may also be employed with the electrodes to achieve different geometries. FIG. 31C shows a fiber membrane fabricated using a collector composed of a close-packed square array of stainless steel beads. FIG. 31D shows a fiber membrane produced using a collector composed of square arrays of stainless steel microbeads with a gradual increase of the inter-electrode distance in one direction. The fiber membranes were not removed from the collectors during SEM imaging and can be readily removed (e.g., peeled off) from collectors as needed.

Figure 32:
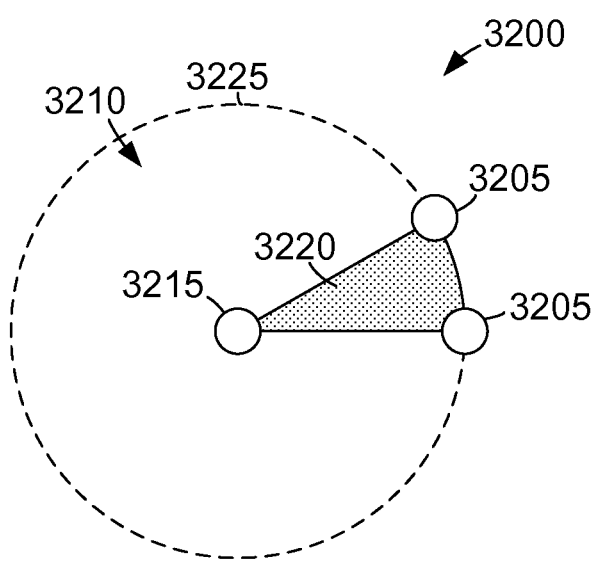
FIG. 32 is a diagram of a collector with peripheral electrodes partially circumscribing an area.

FIG. 32 is a diagram of a collector 3200 with peripheral electrodes 3205 partially circumscribing an area 3210. Collector 3200 also includes an inner electrode 3215. Peripheral electrodes 3205 and inner electrode 3215 define a portion 3220 of area 3210. In exemplary embodiments, peripheral electrodes 3205 are positioned on a perimeter 3225 of area 3210.

In the embodiment shown in FIG. 32, area 3210 is shown as an ellipse (e.g., a circle), and portion 3220 is shown as a sector of the ellipse. It is contemplated that area 3210 may be any geometric or non-geometric shape, such as an ellipse, polygon, oval, rectangle, square, triangle, and/or any rectilinear or curvilinear shape, and that portion 3220 may be any portion of such a shape.

Electrode array fiber structures described herein enable the formation of "dimple" structures within a fiber membrane. Accordingly, the production of such membranes represents a significant advance in that the fiber membranes described possess multiple microwells arranged into variable, ordered geometries. Furthermore, such structures possess unique, three-dimensional microwells capable of physically confining cells seeded on the surface of the scaffold and facilitating the fabrication of cell microarrays. Compared to known approaches to microarray fabrication, the use of fiber membranes may be a simpler and less expensive technique for forming complex cell microarrays for in vitro and in vivo use. Further, experimental results described above demonstrate that the neurites on the site of wells presented random distribution, and that neurites could bridge from one well to another along the aligned fibers in between. A neuronal network developed using such a structure could be used for high-throughput applications in neurotoxicology and neurodevelopmental biology.

While the making and use of various embodiments of the invention are discussed in detail above, the embodiments of the invention provide many applicable inventive concepts that may be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the embodiments of the invention. Terms such as "a," "an" and "the" are not intended to refer to only a singular entity, but include the general class of which a specific example may be used for illustration. The terminology herein is used to describe specific embodiments of the invention, but their usage does not delimit the invention, except as outlined in the claims.

The order of execution or performance of the operations in embodiments of the invention illustrated and described herein is not essential, unless otherwise specified. For example, it is contemplated that executing or performing a particular operation before, contemporaneously with, or after another operation is within the scope of aspects of the invention. Embodiments of the invention may include additional or fewer operations than those disclosed herein.

What is claimed is:

1. A system for producing a structure including a plurality of fibers, the system comprising:
   one or more first electrodes defining an enclosed area having a center;
   a second electrode positioned at the center of the enclosed area, the second electrode comprising a diameter of up to about 5 mm and terminating in a point; and
   a spinneret at a fixed position with respect to the second electrode, the spinneret configured to dispense a polymer while the one or more first electrodes and the second electrode are charged at a first polarity and the spinneret is electrically charged at a second polarity opposite the first polarity,
   wherein the dispensed polymer forms a plurality of fibers extending from the second electrode to the first electrodes.

2. The system of claim 1, wherein the area defines a horizontal plane, and the spinneret is aligned with the second electrode and vertically offset from the horizontal plane.

3. The system of claim 1, wherein the one or more first electrodes comprise a single first electrode that encloses the area.

4. The system of claim 1, wherein the one or more first electrodes comprise a plurality of peripheral electrodes circumscribing the area.

5. The system of claim 1, further comprising a power supply electrically coupled to the one or more first electrodes, the second electrode, and the spinneret, wherein the power supply is configured to:
   electrically charge the one or more first electrodes and the second electrode at the first polarity; and
   electrically charge the spinneret at the second polarity.

6. An apparatus for producing a structure including a plurality of fibers, the apparatus comprising:
   a plurality of first electrodes at least partially circumscribing an area;
   a second electrode positioned within the area and electrically coupled to the first electrodes, the second electrode comprising a diameter of up to about 5 mm and terminating in a point; and
   a power supply electrically coupled to the first electrodes and the second electrode, the power supply configured to electrically charge the first electrodes and the second electrode at a first polarity;

wherein when a spinneret at a fixed position with respect to the second electrode and approximately aligned with the second electrode and charged at a second polarity opposite the first polarity dispenses a polymer, the dispensed polymer forms a plurality of fibers extending from the second electrode to the first electrodes.

7. The apparatus of claim 6, wherein the first electrodes surround the second electrode.

8. The apparatus of claim 6, wherein the first electrodes define a polygon, and the second electrode is positioned within the polygon.

9. The apparatus of claim 6, wherein the first electrodes and the second electrode define a sector of an ellipse.

10. The apparatus of claim 6, wherein the area defines a horizontal plane, and each first electrode of the first electrodes includes a rounded surface oriented toward the horizontal plane.

11. A system for producing a structure including radially aligned fibers, the system comprising:
a first electrode defining an enclosed area;
a second electrode positioned approximately at a center of the enclosed area, the second electrode comprising a diameter of up to about 5 mm and terminating in a point; and
a spinneret at a fixed position with respect to the second electrode, the spinneret configured to dispense a polymer while the first electrode and the second electrode are charged at a first polarity and the spinneret is electrically charged at a second polarity opposite the first polarity;
wherein the dispensed polymer forms a plurality of fibers extending from the second electrode to the first electrode.

12. The system of claim 11, wherein the first electrode comprises a ring defining a circular enclosed area.

13. The system of claim 11, wherein the first electrode defines an enclosed area of between five square centimeters and one hundred square centimeters of variable geometry.

14. The system of claim 11, wherein the enclosed area defines a horizontal plane, and the spinneret is aligned with the second electrode and vertically offset from the horizontal plane.

15. The system of claim 11, further comprising a power supply electrically coupled to the first electrode, the second electrode, and the spinneret, wherein the power supply is configured to:
electrically charge the first electrode and the second electrode at the first polarity; and
electrically charge the spinneret at the second polarity.

16. The system of claim 1, wherein the one or more first electrodes comprise a height ranging from about 0.5 cm to about 2.0 cm.

17. The apparatus of claim 6, wherein the plurality of first electrodes comprise a height ranging from about 0.5 cm to about 2.0 cm.

18. The system of claim 11, wherein the first electrode comprises a height ranging from about 0.5 cm to about 2.0 cm.

19. The system of claim 1, wherein the first electrode is a point electrode or a needle electrode.

20. The system of claim 1, wherein the first electrode is a sphere with a diameter ranging from about 0.5 mm to about 5 mm.

21. The system of claim 6, wherein the first electrode is a point electrode or a needle electrode.

22. The system of claim 6, wherein the first electrode is a sphere with a diameter ranging from about 0.5 mm to about 5 mm.

23. The system of claim 11, wherein the first electrode is one of a point electrode or a needle electrode.

24. The system of claim 11, wherein the first electrode is a sphere with a diameter ranging from about 0.5 mm to about 5 mm.

* * * * *